United States Patent
Wolf et al.

(10) Patent No.: US 12,031,125 B2
(45) Date of Patent: *Jul. 9, 2024

(54) METHOD FOR ISOLATING EXTRACELLULAR NUCLEIC ACIDS USING ANION EXCHANGE PARTICLES

(71) Applicant: QIAGEN GmbH, Hilden (DE)

(72) Inventors: Alexander Wolf, Hilden (DE); Sandra Hammerschmidt, Hilden (DE); Thorsten Voss, Hilden (DE)

(73) Assignee: QIAGEN GmbH, Hilden (DE)

( * ) Notice: Subject to any disclaimer, the term of this patent is extended or adjusted under 35 U.S.C. 154(b) by 88 days.

This patent is subject to a terminal disclaimer.

(21) Appl. No.: 17/385,460

(22) Filed: Jul. 26, 2021

(65) Prior Publication Data

US 2022/0010298 A1 Jan. 13, 2022

Related U.S. Application Data

(63) Continuation of application No. 15/577,692, filed as application No. PCT/EP2016/063252 on Jun. 10, 2016, now Pat. No. 11,104,896.

(30) Foreign Application Priority Data

Jun. 10, 2015 (EP) ..................... 15171466

(51) Int. Cl.
 *C12N 15/10* (2006.01)
 *C12Q 1/6806* (2018.01)

(52) U.S. Cl.
 CPC ....... *C12N 15/101* (2013.01); *C12N 15/1006* (2013.01); *C12N 15/1013* (2013.01); *C12Q 1/6806* (2013.01)

(58) Field of Classification Search
 CPC .............. C12N 15/101; C12N 15/1006; C12N 15/1013; C12Q 1/6806
 USPC ...................................... 435/6.12
 See application file for complete search history.

(56) References Cited

U.S. PATENT DOCUMENTS

| | | | |
|---|---|---|---|
| 7,332,277 B2 | 2/2008 | Dhallan | |
| 7,442,506 B2 | 10/2008 | Dhallan | |
| 8,586,306 B2 | 11/2013 | Fernando | |
| 9,102,935 B2 | 8/2015 | Erbacher et al. | |
| 9,663,779 B2 | 5/2017 | Fabis et al. | |
| 11,104,896 B2 * | 8/2021 | Wolf | C12N 15/101 |
| 2004/0259162 A1 | 12/2004 | Kappel et al. | |
| 2005/0106602 A1 | 5/2005 | Akhavan-Tafti | |
| 2006/0046261 A1 | 3/2006 | Porter et al. | |
| 2007/0105094 A1 | 5/2007 | Fujita et al. | |
| 2007/0185322 A1 | 8/2007 | Akhavan-Tafti | |
| 2008/0003575 A1 | 1/2008 | Michalik et al. | |
| 2009/0018323 A1 | 1/2009 | Erbacher et al. | |
| 2010/0099150 A1 | 4/2010 | Fang et al. | |
| 2010/0184069 A1 | 7/2010 | Fernando et al. | |
| 2010/0209930 A1 | 8/2010 | Fernando | |
| 2011/0054162 A1 | 3/2011 | Kim et al. | |
| 2011/0059547 A1 | 3/2011 | Dehal et al. | |
| 2011/0076751 A1 | 3/2011 | Fabis et al. | |
| 2011/0111410 A1 | 5/2011 | Ryan et al. | |
| 2011/0165676 A1 | 7/2011 | Hopkins | |
| 2011/0319506 A1 | 12/2011 | Erbacher et al. | |
| 2012/0171675 A1 | 7/2012 | Horlitz et al. | |
| 2012/0231446 A1 | 9/2012 | Heckel et al. | |
| 2012/0245337 A1 | 9/2012 | Fabis et al. | |
| 2018/0244707 A1 | 8/2018 | Ritt et al. | |

FOREIGN PATENT DOCUMENTS

| | | |
|---|---|---|
| DE | 10 2008 063 001 A1 | 6/2010 |
| DE | 10 2008 063 003 A1 | 6/2010 |
| EP | 0 726 312 A2 | 8/1996 |
| EP | 0 770 689 A2 | 5/1997 |
| EP | 1 319 716 A1 | 6/2003 |
| EP | 0 880 537 B1 | 12/2004 |
| EP | 1 118 2819 | 9/2011 |
| JP | 6 205 676 A | 7/1994 |
| WO | 95/21849 A1 | 8/1995 |
| WO | 97/34015 A1 | 9/1997 |
| WO | 97/35589 A1 | 10/1997 |
| WO | 99/29703 A2 | 6/1999 |
| WO | 02/48164 A2 | 6/2002 |

(Continued)

OTHER PUBLICATIONS

Applied Biosystems, "DNA Isolation from Fresh and Frozen Blood, Tissue Culture Cells, and Buccal Swabs," URL:http://www3.appliedbiosystems.com/cms/groups/mcb_support/documents/generaldocuments/cms_041387.pdf (55 pages) [retrieved on Feb. 7, 2012].

De Vendittis et al., "A Fluorimetric Method for the Estimation of the Critical Micelle Concentration of Surfactants," *Analytical Biochemistry* 115:278-286, 1981.

De Vries et al., "PCR on Cell Lysates Obtained from Whole Blood Circumvents DNA Isolation," *Clinical Chemistry* 47(9):1701-1702 (2001).

Fan et al., "Analysis of the Size Distributions of Fetal and Maternal Cell-Free DNA by Paired-End Sequencing," *Clinical Chemistry* 56(8), 2010, 8 pages.

Fleischhacker, "Biology of Circulating mRNA—Still More Questions Than Answers?" Ann. N.Y. Acad. Sci. 1075:40-49 (2006).

Fleischhacker et al., "Circulating nucleic acids (CNAs) and cancer—A survey," *Biochimica et Biophysica Acta* 1775:181-232, 2007.

(Continued)

*Primary Examiner* — Yih-Horng Shiao
(74) *Attorney, Agent, or Firm* — Seed IP Law Group LLP

(57) ABSTRACT

The present invention pertains to methods and kits for isolating extracellular nucleic acids from a biological sample using anion exchange particles. It was found that incorporating into the binding mixture a polyoxyalkylene fatty alcohol ether compensates performance variations that are attributable to differences in the anion exchange surface as they may occur e.g. between different lots/batches of the anion exchange particles and/or during storage of said particles. Moreover, including a polyoxyalkylene fatty alcohol ether in the binding mixture resulted in a higher purity of the obtained eluates revealing significantly less inhibition in a downstream reaction such as a PCR reaction.

24 Claims, 7 Drawing Sheets

Specification includes a Sequence Listing.

(56) References Cited

FOREIGN PATENT DOCUMENTS

| | | | |
|---|---|---|---|
| WO | 2006/036243 A2 | 4/2006 |
| WO | 2008/077017 A2 | 6/2008 |
| WO | 2008/152102 A1 | 12/2008 |
| WO | 2009/102632 A2 | 8/2009 |
| WO | 2009/144182 A1 | 12/2009 |
| WO | 2010/072834 A1 | 7/2010 |
| WO | 2013/004710 A2 | 1/2013 |
| WO | 2013/037401 A1 | 3/2013 |
| WO | 2013/045432 A1 | 4/2013 |
| WO | 2013/045434 A1 | 4/2013 |
| WO | 2013/045457 A1 | 4/2013 |
| WO | 2013/045458 A1 | 4/2013 |
| WO | 2014/049022 A1 | 4/2014 |
| WO | 2014/072367 A1 | 5/2014 |
| WO | 2014/146781 A1 | 9/2014 |
| WO | 2015/140218 A1 | 9/2015 |

OTHER PUBLICATIONS

Genov et al., "Stability of subtilisins and related proteinases (subtilases)," *Int. J. Peptide Protein Res.* 45:391-400, 1995.

Helenius et al., "Properties of Detergents," *Methods Enzymol.* 56:734-749, 1979.

Hromadnikova et al., "Quantification of Fetal and Total Circulatory DNA in Maternal Plasma Samples Before and After Size Fractionation by Agarose Gel Electrophoresis," *DNA and Cell Biology* 25(11):635-640, 2006.

Ivancic-Jelecki et al., "Isolation of cell-free DNA from plasma by chromatography on short monolithic columns and quantification of non-apoptotic fragments by real-time polymerase chain reaction," *Journal of Chromatography A* 1216:2717-2724 (2009).

Kirsch et al., "An Improved Method for the Isolation of Free-Circulating Plasma DNA and Cell-Free DNA from Other Body Fluids," *Ann. N.Y. Acad. Sci.* 1137:135-139 (2008).

Melkonyan et al., "Transrenal Nucleic Acids: From Proof of Principle to Clinical Tests," *Ann. N.Y. Acad. Sci.* 1137:73-81 (2008).

Mittal, "Determination of CMC of Polysorbate 20 in Aqueous Solution by Surface Tension Method," *Journal of Pharmaceutical Sciences* 61(8):1334-1335, 1972.

Pandit et al., "Phase behavior of aqueous solutions containing nonionic surfactant-polyethylene glycol mixtures," *International Journal of Pharmaceutics* 122:27-33 (1995).

Shekhtman et al., "Optimization of Transrenal DNA Analysis: Detection of Fetal DNA in Maternal Urine," *Clinical Chemistry* 55(4):723-729 (2009).

Swarup et al., "Circulating (cell-free) nucleic acids—A promising, non-invasive tool for early detection of several human diseases," *FEBS Letters* 581:795-799, 2007.

Zhang et al., "Direct DNA Amplification from Crude Clinical Samples Using a PCR Enhancer Cocktail and Novel Mutans of Taq," *Journal of Molecular Diagnostics* 12(2):152-161 (Mar. 2010).

\* cited by examiner

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Forward primer - h18S rDNA 66 bp amplicon

<400> SEQUENCE: 1
gccgctagag gtgaaattct tg                                             22

<210> SEQ ID NO 2
<211> LENGTH: 21
<212> TYPE: DNA
<213> ORGANISM: Artificial Sequence
<220> FEATURE:
<223> OTHER INFORMATION: Reverse primer - h18S rDNA 66bp amplicon

<400> SEQUENCE: 2
cattcttggc aaatgctttc g                                              21

<210> SEQ ID NO 3
<211> LENGTH: 21

```
<212> TYPE: DNA
<213> ORGANISM: Artificial Sequence
<220> FEATURE:
<223> OTHER INFORMATION: Probe - h18S rDNA 66bp amplicon

<400> SEQUENCE: 3
accggcgcaa gacggaccag a                                                      21

<210> SEQ ID NO 4
<211> LENGTH: 22
<212> TYPE: DNA
<213> ORGANISM: Artificial Sequence
<220> FEATURE:
<223> OTHER INFORMATION: Forward primer - h18S rDNA 500 bp amplicaon

<400> SEQUENCE: 4
gtcgctcgct cctctcctac tt                                                     22

<210> SEQ ID NO 5
<211> LENGTH: 19
<212> TYPE: DNA
<213> ORGANISM: Artificial Sequence
<220> FEATURE:
<223> OTHER INFORMATION: Reverse primer - h18S rDNA 500bp amplicon

<400> SEQUENCE: 5
ggctgctggc accagactt                                                         19

<210> SEQ ID NO 6
<211> LENGTH: 25
<212> TYPE: DNA
<213> ORGANISM: Artificial Sequence
<220> FEATURE:
<223> OTHER INFORMATION: Probe - h18S rDNA 500bp amplicon

<400> SEQUENCE: 6
ctaatacatg ccgacgggcg ctgac                                                  25
```

METHOD FOR ISOLATING EXTRACELLULAR NUCLEIC ACIDS USING ANION EXCHANGE PARTICLES

CROSS REFERENCE TO RELATED APPLICATIONS

The present application is a continuation application of U.S. application Ser. No. 15/577,692 filed Nov. 28, 2017, which is a U.S. national phase application of PCT/EP2016/063252 filed Jun. 10, 2016, which claims priority to EP Application No. 15171466.4 filed Jun. 10, 2015. U.S. application Ser. No. 15/577,692 is herein incorporated by reference in its entity.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025_480C1_SEQUENCE_LISTING.txt. The text file is 2 KB, was created on Jul. 24, 2021 and is being submitted electronically via EFS-Web.

The present invention pertains to methods and kits for isolating extracellular nucleic acids from a biological sample using anion exchange particles.

BACKGROUND OF THE INVENTION

Extracellular nucleic acids have been identified in many sample biological types such as blood, plasma, serum and other body fluids and are of great interest. The analysis of extracellular nucleic acids is of interest in many medical conditions, malignancies and infectious processes inter alia for screening, diagnosis, prognosis, surveillance for disease progression, for identifying potential therapeutic targets, and for monitoring treatment response. Additionally, fetal extracellular nucleic acids present in maternal blood are being analysed for diagnostic or medical purposes, e.g. to determine or analyse the gender identity, genetic disorders such as chromosomal abnormalities and/or to monitor pregnancy-associated complications. Thus, extracellular nucleic acids are in particular useful in non-invasive diagnosis and prognosis and they can be used e.g. as diagnostic or prognostic markers in many fields of application, such as non-invasive prenatal genetic testing, oncology, transplantation medicine or many other diseases. However, extracellular nucleic acids are also found in healthy human beings. Common applications and analysis methods of extracellular nucleic acids are e.g. described in WO97/035589, WO97/34015, Swarup et al, FEBS Letters 581 (2007) 795-799, Fleischhacker Ann. N.Y. Acad. Sci. 1075: 40-49 (2006), Fleischhacker and Schmidt, Biochmica et Biophysica Acta 1775 (2007) 191-232, Hromadnikova et al (2006) DNA and Cell biology, Volume 25, Number 11 pp 635-640; Fan et al (2010) Clinical Chemistry 56:8. Besides mammalian extracellular nucleic acids that derive e.g. from tumor cells or the fetus, cell-containing samples may also comprise other nucleic acids of interest that are not comprised in cells. An important, non-limiting example is pathogen nucleic acids such as viral nucleic acids.

Samples usually contain only a low concentration of extracellular nucleic acids. E.g. in plasma, free circulating nucleic acids are often present in a concentration of only 1-100 ng/ml, even though higher levels can be found in disease conditions such as e.g. cancer. Furthermore, extracellular nucleic acids often circulate as fragments of a size in the range of 100 to 500 nt, in particular 120 to 250 nt (when indicating the size and hence the chain length of a molecule, the term "nt" also includes "bp" in case of DNA). For ccfDNA in plasma, the average length is often only approx. 140-180 bp. Additionally, the actual target extracellular nucleic acid that is supposed to be identified for diagnostic or medical purposes usually also represents only a small fraction within the total extracellular nucleic acids. With respect to ccfDNA, usually only a few thousand amplifiable copies are present per ml blood depending on the circumstances such as e.g. on the pregnancy state or tumor grade. Specifically tumor specific DNA fragments are very rare and often are comprised in a concentration that is 1000-fold less than the "normal" extracellular nucleic acid background. The low concentration poses challenges with respect to the isolation of the extracellular nucleic acids which must be very efficient and robust.

Methods are known in the prior art for isolating extracellular nucleic acids from biological samples, such as in particular plasma samples. Here, also several kits are commercially available. For example, the QIAamp circulating nucleic acid kit (QIAGEN) provides an efficient protocol that allows to process a sample size of up to 5 ml for isolating the extracellular nucleic acids. It essentially requires a manual nucleic acids extraction because of the large process volume (up to 25 ml).

However, it is desirous to provide a method that is suitable for automation. E.g. once a diagnostic target has been established for routine testing, customers require automation to manage higher throughputs e.g. in laboratories. High volume laboratories may e.g. process 250 to 2500 specimens per day have a high demand to avoid manual steps as far as possible and to automate the sample preparation. An automated isolation protocol has significant advantages because it reduces the risks of erroneous results due to errors that occur during the manual nucleic acid isolation.

A method for isolating extracellular nucleic acids that is suitable for automation is described in WO 2013/045432. Extracellular nucleic acids are bound using appropriate pH conditions to a solid phase which comprises anion exchange groups. The solid phase can be provided by magnetic particles. The described method is efficient and can be performed rapidly.

In the field of nucleic acid isolation, it is desirous to provide the materials that are used in the isolation method in a kit format. This requires that the kit materials provide also after storage uniform results when used for nucleic acid isolation. In addition, variations between batches should be avoided in order to ensure that reliable, uniform isolation results are achieved in particular with respect to yield and purity of the isolated nucleic acids. The isolation should preferably be quantitative.

It was found that the isolation of extracellular nucleic acids with anion exchange particles with uniform results is particularly challenging. Even though the nucleic acid binding surface of the anion exchange beads is in strong excess compared to the low amount of extracellular nucleic acids in the sample, it was found that the isolation results varied, even if the same type of reagents and anion exchange beads were used in the same protocol. Despite the excess of available anion exchange surface it was found that quantitative isolation results may strongly depend on the synthesized bead lot (also referred to as batch). Even small variations in the anion exchange surface resulted in strong performance variations with respect to the efficiency of extracellular nucleic acid recovery. That small variations in the anion exchange surface have a noticeable impact on the extracellular nucleic acid yield is probably attributable to the fact that extracellular nucleic acids are contained only in low amounts in samples. Such variations in the anion exchange surface may occur during the standard production process of the anion exchange particles or may occur during storage (also referred to as aging). This is disadvantageous, because excluding such small variations in the anion exchange surface it would require even more stringent controls in the production process of the anion exchange particles, resulting in more wastage what increases the costs. Furthermore, this performance risk disadvantageously reduces the acceptable storage time of the kit.

It is the object of the present invention to provide a method for isolating extracellular nucleic acids from a sample containing extracellular nucleic acids, which avoids at least one of the prior art drawbacks discussed above. In particular, it is an object of the present invention to provide a method for isolating extracellular nucleic acids which is less susceptible to performance variations.

SUMMARY OF THE INVENTION

The present invention pertains to a technology wherein particles providing an anion exchange surface are used for isolating extracellular nucleic acids. The present invention is inter alia based on the surprising finding that incorporating into the binding mixture a specific non-ionic detergent, namely a polyoxyalkylene fatty alcohol ether, compensates performance variations that are attributable to differences in the anion exchange surface as they may occur e.g. between different lots/batches of the anion exchange particles and/or during storage of said particles. This effect is not seen with other non-ionic detergents such as e.g. Triton X-100 or other classes of detergents such as cationic detergents. Moreover, including a polyoxyalkylene fatty alcohol ether in the binding mixture resulted in a higher purity of the obtained eluates revealing significantly less inhibition in downstream reactions, e.g. amplification reactions such as a PCR reaction compared to when other non-ionic detergents such as Triton X-100 were used. Thereby, the invention provides an improved method for isolating extracellular nucleic acids from biological samples using anion exchange particles.

According to a first aspect, the present invention provides a method for isolating extracellular nucleic acids from a biological sample, comprising
(a) preparing from the sample a binding mixture comprising
  i) extracellular nucleic acids;
  ii) particles providing an anion exchange surface;
  iii) at least one non-ionic detergent which is a polyoxyalkylene fatty alcohol ether;
  iv) optionally at least one salt,
  wherein the binding mixture has a pH so that extracellular nucleic acids bind to the particles;
(b) separating the particles with the bound extracellular nucleic acids from the remaining binding mixture;
(c) optionally washing the bound extracellular nucleic acids; and
(d) optionally eluting bound extracellular nucleic acids.

According to a second aspect, a kit for performing the method according to the first aspect is provided, which comprises
(a) a lysis and/or binding composition comprising
  i) at least one non-ionic detergent which is a polyoxyalkylene fatty alcohol ether;
  ii) optionally at least one salt;
  iii) at least one buffer;
  wherein said composition has an acidic pH;
(b) particles providing an anion exchange surface;
(c) optionally a proteolytic enzyme;
(d) optionally one or more wash solutions and
(e) optionally one or more elution solutions.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only.

DETAILED DESCRIPTION OF THE INVENTION

Figure 1:
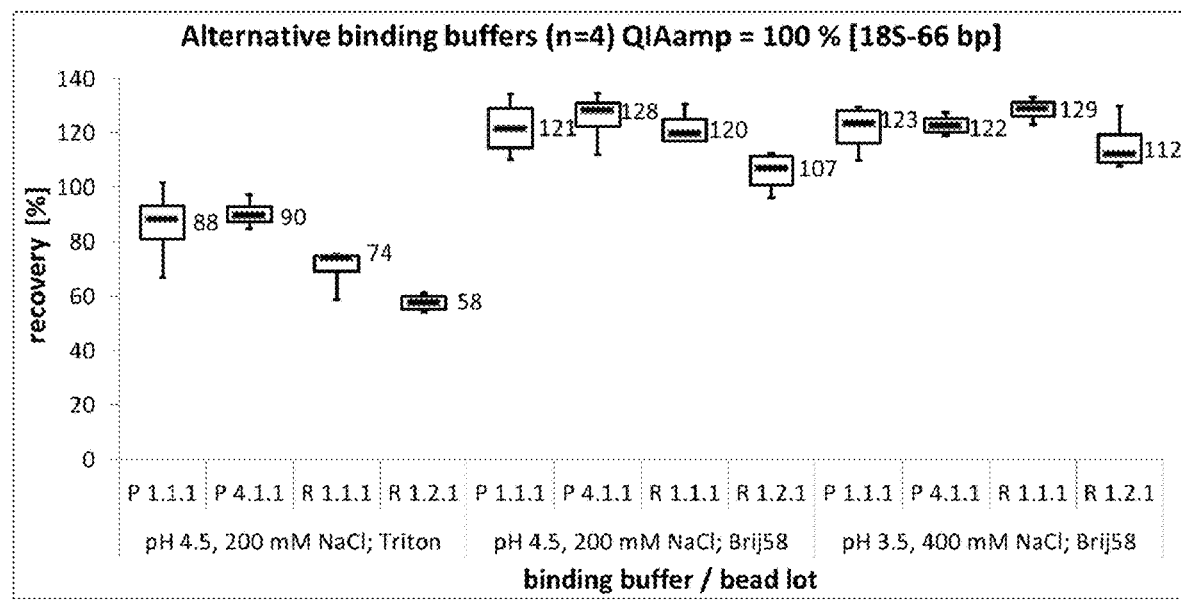
FIG. 1: ccfDNA from 2 ml plasma was extracted using (I) an automated extraction protocol for isolating circulating DNA using magnetic anion exchange particles (comparing different "poor-working" bead lots with Triton X-100 and Brij58 in the binding buffer) and as a reference method (II) the QIAamp Circulating NA Kit. The plasma samples were obtained from blood samples that were stabilized using the product Cell-free DNA BCT (Streck Inc, Cat. No: 218962). Each condition was tested in 4 replicates (n=4). Eluates were subjected to real-time PCR (18S coding sequence; duplex PCR: 66 bp amplicon shown) and ccfDNA recovery was calculated as copies per ml plasma and compared to the manual and ccfDNA recovery was calculated as copies per ml plasma and compared to the manual QIAamp Circulating NA kit (recovery set to 100%). Including a polyoxyethylene fatty alcohol ether as non-ionic detergent, here Brij58, in the binding buffer compensates bead lots showing a reduced ccfDNA affinity. This effect was not seen when using the non-ionic detergent Triton X-100.

The present invention provides an improved technology for isolating extracellular nucleic acids from biological samples using particles providing an anion exchange surface.

Method

According to a first aspect, the present invention provides a method for isolating extracellular nucleic acids from a biological sample, comprising (a) preparing from the sample a binding mixture comprising
  i) extracellular nucleic acids;
  ii) particles providing an anion exchange surface;
  iii) at least one non-ionic detergent which is a polyoxyalkylene fatty alcohol ether;
  iv) optionally at least one salt,
  wherein the binding mixture has a pH so that extracellular nucleic acids bind to the particles,
(b) separating the particles with the bound extracellular nucleic acids from the remaining binding mixture;
(c) optionally washing the bound extracellular nucleic acids; and
(d) optionally eluting bound extracellular nucleic acids.

The present method allows to isolate extracellular nucleic acids with good, uniform yield even if variations in the anion exchange surface of the particles occur. Such variations can occur during the production process and/or during storage of the particles. The present method is suitable for automation and the used materials can be provided in a kit format that is also suitable for long-term storage. Therefore, the method has important advantages. The individual steps and preferred embodiments are explained in the following.

Step (a)—Preparation of the Binding Mixture

In step a) of the present method a binding mixture is prepared from the biological sample that contains extracellular nucleic acids. The binding mixture comprises anion exchange particles for binding the extracellular nucleic acids and additionally comprises at least one non-ionic detergent which is a polyoxyalkylene fatty alcohol ether.

The term "binding mixture" as used herein refers to the composition that is prepared for the nucleic acid binding step and which allows to bind extracellular nucleic acids comprised in the sample to the anion exchange surface of the particles. By preparing the binding mixture, conditions are established so that extracellular nucleic acids comprised in the binding mixture bind to the anion exchange surface of the particles. The binding mixture in particular comprises the biological sample, the anion exchange particles and reagents and/or compounds that were added in order to prepare the sample for the binding step.

An important feature of the invention is the incorporation of at least one polyoxyalkylene fatty alcohol ether as non-ionic detergent in the binding mixture. Polyoxyalkylene fatty alcohol ethers are prepared by alkoxylation, preferably ethoxylation, of fatty alcohols. The polyoxyalkylene fatty alcohol ether may be selected from polyoxyethylene fatty alcohol ethers and polyoxypropylene fatty alcohol ethers, the use of a polyoxyethylene fatty alcohol ether being preferred. Subsequently, embodiments of the invention are in particular described referring to the preferred embodiment, wherein a polyoxyethylene fatty alcohol ether is used. This disclosure applies mutatis mutandis to the use of a polyoxyalkylene fatty alcohol ether in general. In addition, embodiments described herein by referring to a polyoxyalkylene fatty alcohol ether in general in particular relate to and hence refer to the use of a polyoxyethylene glycol fatty alcohol ether.

The term "fatty alcohol" in particular means for the purposes of the present invention alcohols having a chain length of from 6 to 22 carbon atoms. The chain length may be selected from 8 to 20 carbon atoms, 10 to 19 carbon atoms and 12 to 18 carbon atoms. Preference is in particular given to fatty alcohols having a chain length from 14 to 20 carbon atoms, more preferred 15 to 19 carbon atoms or 16 to 18 carbon atoms. Although the fatty alcohol may be mono- or polyunsaturated, it is preferably a saturated fatty alcohol.

The term "polyoxyethylene" in particular means for the purposes of the present invention an —(CH2CH2O)n unit, in particular an HO—(CH2CH2O)n unit, with n being preferably an integer from 2 to 150, such as an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 and 150. Preferably, n is in a range selected from 4 to 120, 8 to 80, 10 to 60 and 12 to 50.

Preferred examples of suitable polyoxyethylene fatty alcohol ethers are polyethoxylated lauryl, cetyl, oleyl or stearyl alcohols which may be used alone or in combination. According to one embodiment, the at least one polyoxyethylene fatty alcohol ether comprises a fatty alcohol component having from 6 to 22 carbon atoms and a polyoxyethylene component having from 2 to 150 (CH2CH2O) units. According to one embodiment, the polyoxyethylene fatty alcohol ether is selected from the group consisting of polyoxyethylene(2) cetyl ether, polyoxyethylene(10) cetyl ether, polyoxyethylene(20) cetyl ether, polyoxyethylene(2) stearyl ether, polyoxyethylene(10) stearyl ether, polyoxyethylene(20) stearyl ether, polyoxyethylene(2) oleyl ether, polyoxyethylene(10) oleyl ether, polyoxyethylene(20) oleyl ether and polyoxyethylene(100) stearyl ether. The numbers indicate the average number of ethylene oxide units. Particularly suitable are polyoxyethylene fatty alcohol ethers sold under the trade name Brij®, for example by ICI Surfactants.

A polyoxyethylene cetyl, polyoxyethylene oleyl or polyoxyethylene stearyl alcohol ethers can be selected from the group comprising polyoxyethylene(2) cetyl ether (Brij® 52), polyoxyethylene(10) cetyl ether (Brij® 56), polyoxyethylene(20) cetyl ether (Brij® 58), polyoxyethylene(2) stearyl ether (Brij® 72), polyoxyethylene(10) stearyl ether (Brij® 76), polyoxyethylene(20) stearyl ether (Brij® 78), polyoxyethylene(2) oleyl ether (Brij® 92), polyoxyethylene(10) oleyl ether (Brij® 97), polyoxyethylene(20) oleyl ether (Brij® 98) and polyoxyethylene(100) stearyl ether (Brij® 700). Polyoxyethylene cetyl, polyoxyethylene oleyl or polyoxyethylene stearyl alcohol ethers may also be used as powders, for example polyoxyethylene(21) stearyl ether powder (Brij® 721P).

According to one embodiment, the polyoxyalkylene fatty alcohol ether is selected from polyoxyethylene cetyl, polyoxyethylene oleyl and polyoxyethylene stearyl alcohol ethers and is preferably selected from the group consisting of polyoxyethylene(10) cetyl ether (Brij® 56), polyoxyethylene(20) cetyl ether (Brij® 58), polyoxyethylene(20) stearyl ether (Brij® 78) and polyoxyethylene(20) oleyl ether (Brij® 98). The use of a polyoxyethylene(20) cetyl ether is particularly preferred.

Detergents are amphipathic in nature and contain a polar group at one end and a hydrophobic carbon chain at the other end. Micellization occurs when surface-active compounds form non-covalent clusters in solution this process is driven by hydrophobic effects. Micellization is a critical phenomenon when considering detergent applications. Each detergent can be characterized by its critical micelle concentration (CMC); the concentration of detergent above which monomers self-assemble into non-covalent aggregates, which are called micelles (see Rosen, Surfactants and interfacial phenomena, third edition, 2004; Helenius et al., Properties of detergents. Methods Enzymol, 1979, 56:p 734-49 and Mukerjee et al., Critcal micelle concentrations of aqueous surfactants systems, vol. NSRDS-NBS 36. 1970). The CMC actually does not occur at a single concentration, but rather, over a narrow concentration range. When the total detergent concentration is below the CMC, detergent monomers are free in bulk solution. However, as more detergent is added above the CMC, the additional detergent monomers will go into micelles. Detergent micelles are dynamic structures; detergent monomers within the micelles are in constant, rapid exchange, with pre-detergent monomers in solution. The CMC can be determined by a variety of methods including surface tension measurements (see Mittal, Determination of CMC of polysorbate 20 in aqueous solution by surface tension method. J Pharm Sci, 1972. 61(8):p. 1334-5) and dye (e.g. annilino-1-naphtalene sulfonic acid [ANS] binding experiments (see De Vendittis et al., A fluorometric method for the estimation of the critical micelle concentration of surfactants, Anal Biochem, 1981, 115:p. 278-286). The hydrophobic group of the detergent effects the CMC. The CMC usually decreases as the number of carbon atoms in alkyl chain increases up to approximately 16 to 18 carbons for straight chain alkyls.

It was found that using a polyoxyalkylene fatty alcohol ether with a low CMC is beneficial. According to one embodiment, the polyoxyalkylene fatty alcohol ether has a CMC of 0.15 mM or less. According to one embodiment, it has a CMC of 0.125 mM or less, 0.12 mM or less, 0.115 mM or less, 0.1 mM or less, 0.095 mM or less, 0.90 mM or less or 0.085 mM or less. A CMC of 0.1 mM or less is preferred. CMC ranges include but are not limited to 0.005 to 0.15 mM, 0.01 to 0.125 mM, 0.015 mM to 0.12 mM, 0.02 mM to 0.115 mM, 0.025 mM to 0.1 mM, 0.03 mM to 0.095 mM and 0.035 mM to 0.09 mM. E.g. the preferred embodiment polyoxyethylene(20) cetyl ether has a CMC of approx. 0.08 mM. According to one embodiment, the CMC lies in the range of 0.05 mM to 0.09 mM.

According to one embodiment, the binding mixture comprises the at least one polyoxyalkylene fatty alcohol ether in a concentration selected from 0.05% to 15%, 0.75% to 12%, 0.1% to 10%, 0.125% to 8%, 0.15% to 7.5%, 0.175% to 6.5% and 0.2% to 6%. Particularly suitable is a concentration in the range of 0.1% to 5% and 0.1% to 2% as is demonstrated by the examples. In case more than one polyoxyalkylene fatty alcohol ether is comprised in the binding mixture, the indicated concentration ranges refer according to one embodiment to the total concentration of comprised polyoxyalkylene fatty alcohol ethers.

The particles provide an anion exchange surface. Thus, they comprise anion exchange groups at their surface. The anion exchange groups may be of the same type, however, different types of anion exchange groups may also be used. Examples of such anion exchange groups are monoamines, diamines, polyamines, and nitrogen-containing aromatic or aliphatic heterocyclic groups. Preferably, the anion exchange group comprises at least one amino group, e.g. a primary, secondary, tertiary or quarternary amino group. In preferred embodiments, the anion exchange group com prises a group selected from the group consisting of primary, secondary and tertiary amines, more preferably of the formula

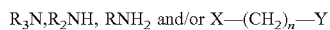
$R_3N, R_2NH, RNH_2$ and/or $X-(CH_2)_n-Y$ wherein
X is $R_2N$, RNH or $NH_2$,
Y is $R_2N$, RNH or $NH_2$,
R is independently of each other a linear, branched or cyclic alkyl, alkenyl, alkynyl or aryl substituent which may comprise one or more heteroatoms, preferably selected from O, N, S and P, and
n is an integer in the range of from 0 to 20, preferably 0 to 18.

Hence, the anion exchange groups may have a protonatable group and optionally may have more than one protonatable group which may be the same or different. A protonatable group preferably is a chemical group which is neutral or uncharged at a high pH value and is protonated at a low pH value, thereby having a positive charge. In particular, the protonatable group is positively charged at the binding pH at which binding of the extracellular nucleic acid to the particles occurs. Preferably, the pKa value of the (protonated) protonatable group is in the range of from about 8 to about 13, more preferably from about 8.5 to about 12 or from about 9 to about 11.5.

Examples of suitable anion exchange groups are in particular amino groups such as primary, secondary and tertiary amino groups as well as cyclic amines, aromatic amines and heterocyclic amines, preferably tertiary amino groups. The amino groups preferably bear alkyl, alkenyl, alkynyl and/or aromatic substituents, including cyclic substituents and substituents which together with the nitrogen atom form a heterocyclic or heteroaromatic ring. The substituents preferably comprise 1 to 20 carbon atoms, more preferably 1 to 12, 1 to 8, 1 to 6, 1 to 5, 1 to 4, 1 to 3 or 1 or 2 carbon atoms. They may be linear or branched and may comprise heteroatoms such as oxygen, nitrogen, sulfur, silicon and halogen (e.g. fluorine, chlorine, bromine) atoms. Preferably, the substituents comprise not more than 4, more preferably not more than 3, not more than 2 or not more than 1 heteroatom.

In one embodiment the anion exchange group preferably carries 1 to 10 amino groups. More preferably the anion exchange groups carries 2 to 8, and particularly the anion exchange group carries 2 to 6 amino groups.

Examples of amine functions are primary amines such as aminomethyl (AM), aminoethyl (AE), aminoalkyl, alkylaminoalkyl, dialkylaminoalkyl such as diethylaminoethyl (DEAE), ethylendiamine, diethylentriamine, triethylentetraamine, tetraethylenpentaamine, pentaethylenhexaamine, trimethylamino (TMA), triethylaminoethyl (TEAE), linear or branched polyethylenimine (PEI), carboxylated or hydroxyalkylated polyethylenimine, jeffamine, spermine, spermidine, 3-(propylamino)propylamine, polyamidoamine (PAMAM) dendrimers, polyallylamine, polyvinylamine, N-morpholinoethyl, polylysine, and tetraazacycloal kanes.

Preferably, the particles used comprise dialkylamino groups, especially diethylamino groups, wherein the particles may also comprise more than one type of dialkylamino groups.

Anion exchange particles that can be used in the context of the present invention include, but are not limited to, particulate materials that are functionalized with anion exchange groups. As basic material for the particles, any material suitable for anion exchange chromatography may be used, including but not limited to silicon containing materials such as silica and polysilicic acid materials, borosilicates, silicates, anorganic glasses, organic polymers such as poly(meth)acrylates, polyurethanes, polystyrene, agarose, polysaccharides such as cellulose, metal oxides such as aluminum oxide, magnesium oxide, titanium oxide and zirconium oxide, metals such as gold or platinum, sephadex, sepharose, polyacrylamide, divinylbenzene polymers, styrene divinylbenzene polymers, dextrans, and derivatives thereof; glass or silica. In embodiments, the particles are made of or contain a mineral or polymeric material such as silica, glass, quartz, polyethylene, polypropylene, polyvinylidene fluoride, polyacrylonitrile, polyvinylchloride, polyacrylade, methacrylate or methyl methacrylate. Important is that the particles comprise anion exchange groups at their surface and hence provide an anion exchange surface for interaction with the extracellular nucleic acids. Such surface can be provided by functionalizing the basic material of the particles with suitable anion exchange groups. For functionalizing particles with anion exchange groups in order to provide an anion exchange surface, several methods are feasible and known to the skilled person. The anion exchange groups may be bound directly to the surface of the particles, either covalently or non-covalently, electrostatically and/or may form part of a polymer or other composition which forms a surface coating or which is provided at the surface of the particles. The anion exchange groups may also be precipitated on the particles. According to one embodiment, the anion exchange groups are applied in form of a coating on the particles. A covalent attachment of the anion exchange groups is preferred. The particles may comprise at their surface functionalities for attachment of the anion exchange groups, for example functionalities such as Si—O—Si, Si—OH, alcohol, diol or polyol, carboxylate, amine, phosphate or phosphonate. The anion exchange groups may be attached to the solid phase, for example, by using epoxides, (activated) carboxylic acids, silanes, acid anhydrides, acid chlorides, formyl groups, tresyl groups or pentafluorophenyl groups. The functional groups may be attached directly to the solid phase or via (linear or branched) spacer groups, e.g. hydrocarbons such as —$(CH_2)_n$— groups, carbohydrates, polyethylenglycols and polypropylenglycols. Alternatively, also a polymer composed of monomers comprising the anion exchange group such as an amino functional group can be used as anion exchange material. In certain embodiments, the particles have a silicon containing surface such as a polysilicic acid surface and the anion exchange groups are coupled to said surface by using suitable organosilanes such as an aminosilane.

The anion exchange group may comprise a protonatable group attached to a linker structure. The linker preferably is a linear, branched or cyclic alkylen, alkenylen or alkynylen group which preferably comprises 1 to 20 carbon atoms, more preferably 1 to 12, 1 to 8, 1 to 6, 1 to 5, 1 to 4, 1 to 3 or 1 or 2 carbon atoms. It may further comprise heteroatoms such as oxygen, nitrogen, sulfur, silicon and halogen (e.g. fluorine, chlorine, bromine) atoms, preferably not more than 4, more preferably not more than 3, not more than 2 or not more than 1 heteroatom. In preferred embodiments, the linker group is an alkylene group, in particular a propylene group.

According to one embodiment, the particles comprise a silicon containing surface, preferably a polysilicic acid surface which is derivatized with a silane compound comprising at least one anion exchange group. Suitable methods involving the use of organosilanes such as aminosilanes are well-known.

The particles are preferably spherical. The particles may have a mean diameter selected from the ranges of 100 nm to 35 µm, 150 nm to 30 µm, 200 nm to 25 µm, 250 nm to 20 µm, 300 nm to 15 µm, 350 nm to 10 µm, 400 nm to 7.5 µm, 450 nm to 5 µm, 500 nm to 3 µm, 550 nm to 2.5 µm, 600 nm to 2 µm and 650 nm to 1.75 µm. Particularly preferred ranges include but are not limited to 100 nm to 10 µm, 150 nm to 7.5 µm, 200 nm to 5 µm, 300 nm to 4 µm, 500 nm to 3.5 µm, 550 nm to 2 µm and 600 nm to 1.5 µm. Particles of the respective sizes and in particular of a smaller size such as 10 µm or less, 7.5 µm or less, preferably 5 µm or less, 2.5 µm or less or 1.5 µm or less are easy to handle and can be well resuspended in the binding mixture. Furthermore, respective small particles provide a large surface area that can bind and accordingly can efficiently collect the extracellular nucleic acids from the binding mixture.

When performing the binding step, the anion exchange particles are not comprised in a column or other device that would prevent the particles from moving in the binding mixture but the particles can move in the binding mixture, e.g. when the binding mixture is agitated. Therefore, the particles must be collected from the binding mixture to recover the bound extracellular nucleic acids. According to one embodiment, the particles are magnetic. This simplifies the processing of the particles because they can be processed by the aid of a magnet which is advantageous for automation. The particles may have ferrimagnetic, ferromagnetic, paramagnetic or superparamagnetic properties and preferably are superparamagnetic. Such properties can be achieved by incorporating a suitable magnetic material into the particles. Suitable methods are known to the skilled person. Preferably, the magnetic material is completely encapsulated e.g. by the silica, polysilicic acid, glass or polymeric material that is used as base material for the particles. In certain preferred embodiments, the nucleic acid binding matrix is a silicon containing particle, preferably a polysilicic acid particle, preferably a magnetic polysilicic acid particle which carries anion exchange groups.

Examples of suitable particles and anion exchange groups are described in WO 2010/072834 A1, DE10 2008 063 001A1, WO2010072821A1, DE 10 2008 063 003 and WO 99/29703 to which it is referred.

The anion exchange particles are added in an amount so that the binding capacity of the anion exchange surface is in excess of the nucleic acids contained in the sample. This supports a quantitative isolation of extracellular nucleic acids. Non-limiting examples of suitable amounts of particles (in mg) per ml sample include 0.15 mg to 10 mg, 0.25 mg to 5 mg, 0.5 mg to 3.5 mg, 0.75 mg to 3 mg, 1 mg to 2.5 mg and 1.25 mg to 2 mg. The suitable amount inter alia depends on the sample volume to be processed and the anion exchange particles used and can be determined by the skilled person.

The binding mixture has a pH that allows binding of the extracellular nucleic acids to the anion exchange surface of the particles. The pH of the binding mixture is also referred to as "binding pH" herein. At the binding pH, the anion exchange groups are charged such that they can interact with and thus bind the nucleic acids. The pH that is suitable for binding in particular depends on the nature of the anion exchange groups. Suitable pH values for the binding pH can be determined by the skilled person. According to one embodiment, the binding pH is below the pKa value of a protonatable group of the anion exchange groups. If the anion exchange groups comprise more than one type of protonatable group, the binding pH is below the pKa of at least one protonatable group, preferably all protonatable groups. Preferably, the binding pH is at least 0.5 units below the pKa value, more preferably at least 1 unit, at least 1.5 units, at least 2 units, at least 2.5 units, and most preferably at least 3 units below said pKa value.

The binding mixture may have a pH selected from 7, 6.5, 6.25 and 6. According to one embodiment, the binding pH is in the range of from 3 to 7, more preferably is in a range selected from 3.5 to 6.5; 4 to 6.25; 4.25 to 6 and 4.5 to 5.75. An acidic pH value is advantageous, because it enhances binding and may furthermore, support the release of extracellular nucleic acids such as e.g. DNA that may be trapped e.g. in histone complexes.

According to one embodiment, preparation of the binding mixture comprises adjusting the pH of the sample to the binding pH. This can be achieved by adding acidifying compounds and/or reagents. Suitable examples of acidifying reagents include but are not limited to acids, acidic buffering agents such as carboxylic acids, e.g. acetic acid, sodium acetate/acetic acid buffers, citric acid/citrate buffers, maleic acid, malonic acid, tartaric acid, HCl, HClO$_4$, HClO$_3$, formic acid, boric acid, H$_2$SO$_4$, H$_2$SO$_3$, acidic phosphoric acid/phosphate buffer systems, MES or other water-soluble inorganic or organic acids. The acidifying compound can be included in a lysis and/or binding composition that is contacted with the sample in order to establish the binding conditions in the binding mixture.

In order to maintain the binding pH, it is preferred that the binding mixture comprises a buffer. Depending on the buffer used, the buffer may serve at the same time as acidifying compound in order to establish acidic conditions in the binding mixture. Suitable buffers include but are not limited to carboxylic acid based buffers, phosphoric acid based buffers, phosphate buffers and amino acid based buffers such as glycine, glutamate/glutamine, aspartate/asparagine. These type of buffers were found to work well in the method of the invention, other buffer systems can also be determined by the skilled person. The use of carboxylic acids such as e.g. acetic acid, sodium acetate/acetic acid buffers, citric acid/citrate buffers, maleic acid, malonic acid and tartaric acid and in particular citric acid is preferred. The buffer can be included in a lysis and/or binding composition and hence a reagent that is contacted with the sample in order to establish the binding conditions in the binding mixture.

The binding mixture may comprise a salt. Incorporating a salt into the binding mixture improves the isolation results. According to one embodiment, the salt is an alkali metal salt or an ammonium salt. The alkali metal salt is according to one embodiment an alkali metal halide. Suitable examples include sodium chloride, potassium chloride and lithium chloride, wherein sodium and potassium chloride being preferred. According to one embodiment, sodium chloride is used. The salt may be comprised in the binding mixture in a concentration selected from 50 mM to 1.5M, 75 mM to 1M, 100 mM to 750 mM, 125 mM to 500 mM and 150 mM to 350 mM. When using salt concentrations of e.g. 750 mM and higher, it can be advantageous to use a pH of 5 or less, preferably 4.5 or less. Particularly preferred is a salt concentration in the range of 50 mM to 750 mM or 75 mM to 500 mM. The salt can be included in a lysis and/or binding composition that is contacted with the sample in order to establish the binding conditions in the binding mixture.

According to one embodiment, the binding mixture does not comprise a chaotropic salt such as guanidinium salts, iodides, thiocyanates, perchlorates or other chaotropic salts of equal or stronger chaotropic nature in a concentration of 500 mM or more, 200 mM or more or 100 mM or more. Preferably, the binding mixture lacks such chaotropic salt. This supports to prevent unwanted protein precipitations which could e.g. unspecifically bind to the particles or co-precipitate circulating DNA which would be disadvantageous for the yield. A lack of chaotropic salts as mentioned above is in particular an advantage when being confronted with protein rich samples such as e.g. blood plasma.

According to a preferred embodiment, the binding mixture furthermore comprises a proteolytic enzyme. A proteolytic enzyme is an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Exemplary subtilisins include but are not limited to proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferably, the proteolytic enzyme is proteinase K. Incorporating a proteolytic enzyme was found to improve the purity of the obtained eluate. In particular, the amount of protein contaminations is significantly reduced. In addition, it was found that the use of a proteolytic enzyme increases the extracellular nucleic acid yield. This is in particular seen in case a stabilized sample is processed, e.g. a sample that was stabilized involving the use of a formaldehyde releaser. The method is highly efficient when isolating e.g. cell-free DNA from samples stabilized with Cell-free DNA BCT (Streck) as is demonstrated by the examples. The enzyme is preferably not included in the lysis and/or binding composition but is added separately.

According to one embodiment, the binding mixture is prepared by contacting the sample with a composition and hence a reagent which comprises the at least polyoxyalkylene fatty alcohol ether. Said composition may optionally comprise a salt and/or a buffer. Details regarding the salt and the buffer were described above. The components of the lysis/binding composition are incorporated in and hence are present in the binding mixture. The composition thus assists to prepare the binding conditions and additionally, can support the digestion of the sample to render the extracellular nucleic acids accessible for binding. Therefore, the composition can serve as lysis and/or binding composition (also referred to herein in short as lysis/binding composition or lysis/binding reagent). The terms "digestion" and "lysis" are used interchangeably herein and refer to the digestion of a cell containing sample as well as to the digestion of a cell-depleted or cell-free sample. The digestion or lysis supports that the extracellular nucleic acids are rendered accessible for binding, e.g. by releasing them from associated proteins or other components. Preferably, said composition is an aqueous solution and has an acidic pH value. This embodiment is favorable, because it allows to establish the binding conditions in the binding mixture including the binding pH simply by adding the composition to the sample. The pH of the composition can lie in a range selected from 3 to 6.5, 3.5 to 6 and 4 to 5.5. The pH of the composition is preferably such that when the composition is incorporated into the binding mixture a binding pH as described herein is established. It is preferred that the composition comprises a buffer to maintain the pH. Details of the lysis and/or binding composition are also described in conjunction with the kit according to the second aspect and it is referred to the respective disclosure which also applies here.

According to one embodiment, the lysis and/or binding composition is added to sample in an amount that is suitable to establish the binding conditions. In order to keep the processing volume low and include a high amount of sample in the binding mixture, it is preferred that the sample makes up at least 50%, at least 60%, preferably at least 70%, more preferred at least 75% or at least 80% of the binding mixture The lysis and/or binding composition can be added e.g. in a ratio selected from 1:25 to 1:2, 1:20 to 1:3, 1:15 to 1:6 and 1:10 to 1:4 depending on its composition.

The sample, the anion exchange particles and the lysis and/or binding composition can be contacted or added in any order to prepare the binding mixture. As discussed herein, the sample may be degraded in the lysis/binding composition before the anion exchange particles are added and/or it can be degraded in the binding mixture and hence in the presence of the anion exchange particles. In addition, a proteolytic enzyme can be added e.g. to the sample. The proteolytic enzyme can be contacted with the sample e.g. before, after or at the same time as the lysis/binding composition and/or can be added before, after or at the same time as the anion exchange particles.

According to one embodiment, the sample is contacted with the lysis/binding composition and optionally, but preferably, a proteolytic enzyme in order to digest the sample. The resulting composition can be incubated in order to digest the sample. Such digestion step supports the release of extracellular nucleic acids, for example from proteins or other components that are associated with the extracellular nucleic acids. Thereby, the extracellular nucleic acids can be rendered accessible for nucleic acid binding. After said digestion step, the anion exchange particles can be added in order to prepare the binding mixture.

In an alternative embodiment, the binding mixture is prepared by
  forming a suspension by contacting the anion exchange particles with a composition which comprises the at least one polyoxyalkylene fatty alcohol ether and which optionally comprises a salt and/or a buffer;
  contacting the suspension with the biological sample comprising extracellular nucleic acids;
  optionally adding a proteolytic enzyme prior to, at the same time or after the sample was contacted with the suspension.

This embodiment has significant advantages. The biological sample comprising the extracellular nucleic acids is added after the suspension comprising the lysis/binding composition and the anion exchange particles was provided. This reduces handling steps that are in contact with the sample and thereby reduces contamination risks. According to a preferred embodiment, the proteolytic enzyme is incorporated into the suspension before said suspension is contacted with the sample. The proteolytic enzyme, the composition, which preferably is a lysis and/or binding composition as described above, and the anion exchange particles can be added in any order in order to prepare the suspension. As is demonstrated by the examples, digestion of the sample can occur within the binding mixture.

Binding occurs for a time sufficient to allow substantial binding of the extracellular nucleic acids to the anion exchange particles. The binding mixture may be incubated for binding of the extracellular nucleic acids to the anion exchange particles. The suitable, respectively necessary incubation time depends on the type and amount of particles and anion exchange groups used, the sample volume and the concentration of extracellular nucleic acids in the sample. E.g. shorter incubation times can be sufficient, if particles are used which have a high density of anion exchange groups and hence, are capable of quickly and tightly binding the extracellular nucleic acids. Longer incubation times ensure that the nucleic acids bind highly efficient to the anion exchange particles, thereby allowing to maximize the extracellular nucleic acid recovery from the sample. The binding mixture may be incubated e.g. for two minutes to one hour, preferably 5 minutes to 45 minutes, more preferred 10 minutes to 35 minutes, more preferred 15 to 30 minutes. The binding mixture may be agitated during incubation. A prolonged incubation step is in particular advantageous, in case the sample was not lysed prior to contacting with the anion exchange particles. In this embodiment, digestion of the sample and binding of the released extracellular nucleic acids essentially occur in the same processing step. An incubation time of at least 10 or at least 15 min is advantageous in case a proteolytic enzyme is employed, because this promotes the thorough digestion of proteins contained in the sample. The binding mixture may be agitated during said incubation step.

When using a proteolytic enzyme to support the digestion of the sample, it is common in the art to support the activity of the proteolytic enzyme (e.g. proteinase K) by heating e.g. at a temperature in the range of 35° C. to 65° C., e.g. 40° C. to 55° C. Even though such heating step can be performed in the method of the invention, it was surprisingly found and is shown in the examples that the isolation results are considerably improved if no heating step is performed during digestion but wherein digestion occurs at room temperature. Therefore, improved results are obtained if the digestion and preferably also the binding step is performed at room temperature. More preferably, all steps (a) to (d) of the method occur without heating and hence at room temperature.

The sample is a biological sample which comprises extracellular nucleic acids. A biological sample is obtained from a biological source. The sample is not an artificial sample with synthetically produced nucleic acids but is obtained from a biological source. Biological samples usually have a complex composition and comprise many different components what makes the nucleic acid isolation with sufficient purity challenging. The biological sample may be e.g. selected from the group consisting of body fluids, whole blood, plasma, serum, sputum, lachrymal fluid, lymphatic fluid, synovial fluid, pleural effusion, urine, sweat, liquor, cerebrospinal fluid, ascites, milk, stool, bronchial lavage, saliva, amniotic fluid, nasal secretions, vaginal secretions, a surface biopsy, sperm, semen/seminal fluid, wound secretions and excretions, and cell culture supernatants and supernatants obtained from other swab samples. According to one embodiment, the sample is a body fluid, a body secretion or body excretion, preferably a body fluid or a sample that is derived from a body fluid that comprises extracellular nucleic acids. Most preferably, the sample is whole blood, plasma or serum. Other examples of samples that can be processed with the method according to the present invention include but are not limited to biological samples cell suspensions, cell cultures, supernatant of cell cultures and the like, which comprise extracellular nucleic acids. A biological sample in particular is a natural sample, e.g. obtained from a human or animal or derived from cell culture. The biological sample can be stabilized.

Stabilized samples are also encompassed be the term biological sample and also by the term natural sample. Furthermore, cells may have been removed from the original sample. Respective cell-depleted or cell-free samples are also encompassed by the term biological sample and also by the term natural sample. Typical examples of respective natural samples are body fluids such as blood and samples derived from a body fluid, in particular samples that derive from a body fluid by removing cells from the body fluid.

According to one embodiment, the biological sample comprising the extracellular nucleic acids is a cell-free or cell-depleted sample. A respective cell-free or cell-depleted biological sample can be obtained e.g. from a cell-containing sample by using appropriate technologies to remove cells. A typical example is blood plasma or blood serum which can be obtained from whole blood. If the sample comprises large amounts of cells as is e.g. the case with whole blood, the cells are separated from the remaining sample in order to obtain a cell-free, respectively cell-reduced fraction of the sample which comprises the extracellular nucleic acids. Thus, according to one embodiment, cells are removed from the cell-containing sample to provide the cell-free or cell-depleted sample which comprises the extracellular nucleic acids and from which the extracellular nucleic acids are isolated using the method according to the present invention. This cell removal step is only optional and e.g. may be obsolete if samples are processed (respectively are obtained for processing) which merely comprise minor amounts of residual cells such as e.g. plasma or serum. However, in order to improve the results it is preferred that also respective remaining cells (or potentially remaining cells) are removed as they might contaminate the extracellular nucleic acid population during the isolation. Depending on the sample type, cells, including residual cells, can be separated and removed e.g. by centrifugation, preferably high speed centrifugation, or by using means other than centrifugation, such as e.g. filtration, sedimentation or binding to surfaces on (optionally magnetic) particles if a centrifugation step is to be avoided. Respective cell removal steps can also be easily included into an automated sample preparation protocol. Respectively removed cells may also be processed further e.g. in order to analyse the intracellular nucleic acids. The cells can e.g. be stored and/or biomolecules such as e.g. nucleic acids or proteins can be isolated from the removed cells.

The present method is particularly suitable for processing biological samples which comprise low amounts of extracellular nucleic acids. Good nucleic acid yields are achieved even if the nucleic acid concentration in the sample is very low. As discussed in the introduction, extracellular nucleic acids are depending on the sample often comprised in the samples (such as e.g. a plasma or serum sample) in rather low amounts of 1 to 100 ng/ml sample, even though plasma of e.g. cancer patients can comprise higher amounts. According to one embodiment, the sample containing the nucleic acid comprises nucleic acids in a concentration selected from 2.5 µg/ml sample or less, 2 µg/ml sample or less, 1.5 µg/ml sample or less, 1 µg/ml sample or less, 750 ng/ml sample or less, 500 ng/ml sample or less, 300 ng/ml sample or less, 200 ng/ml sample or less, 150 ng/ml sample or less and 100 ng/ml sample or less.

The sample may constitute a stabilized sample and hence a sample that has been stabilized by appropriate agents. Examples are described herein.

The term "extracellular nucleic acids" or "extracellular nucleic acid" as used herein, in particular refers to nucleic acids that are not contained in cells. Respective extracellular nucleic acids are also often referred to as cell-free nucleic acids. These terms are used as synonyms herein. Hence, extracellular nucleic acids usually are present exterior of a cell or exterior of a plurality of cells within a sample. The term "extracellular nucleic acids" refers e.g. to extracellular RNA as well as to extracellular DNA and mixtures thereof. Examples of typical extracellular nucleic acids that are found in the cell-free fraction (respectively portion) of a biological sample such as a body fluid or a sample derived from a body fluid such as e.g. blood plasma include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogenic nucleic acids released into the extracellular nucleic acid population e.g. from prokaryotes (e.g. bacteria), viruses or fungi. According to one embodiment, the extracellular nucleic acids are obtained from a body fluid or a sample derived from a body fluid as biological sample such as e.g. blood, plasma, serum, saliva, urine, liquor, cerebrospinal fluid, sputum, lachrymal fluid, sweat, amniotic or lymphatic fluid; preferably the extracellular nucleic acids are obtained from the cell-free or cell-depleted portion of the foregoing samples. According to one embodiment, the term extracellular nucleic acid in particular refers to mammalian extracellular nucleic acids, preferably disease-associated or disease-derived extracellular nucleic acids such as tumor-associated or tumor-derived extracellular nucleic acids, extracellular nucleic acids released due to inflammations or injuries, in particular traumata, extracellular nucleic acids related to and/or released due to other diseases, or extracellular nucleic acids derived from a foetus. The term "extracellular nucleic acids" or "extracellular nucleic acid" as described herein also refers to extracellular nucleic acids obtained from other samples, in particular biological samples other than body fluids. Herein, we refer to extracellular nucleic acids that are obtained from a circulating body fluid or a sample derived from a circulating body fluid, in particular from the cell-free or cell-depleted portion of a circulating body fluid as circulating extracellular or circulating cell-free (ccf) nucleic acids. According to one embodiment, extracellular DNA is isolated, in particular circulating cell-free DNA.

At the end of step a), extracellular nucleic acids contained in the binding mixture are bound to the anion exchange particles.

Step (b)—Separation

In step (b) the particles with the bound extracellular nucleic acids are separated from the remaining binding mixture. Thereby, the particles with the bound extracellular nucleic acids are collected. For this purpose, any means known in the art can be used. Suitable means include but are not limited to magnetic separation if magnetic particles are used, centrifugation e.g. if non-magnetic particles are used, sedimentation, the application of a vacuum, filtration and the like.

Step (c)—Washing

After step (b), one or more washing steps may optionally be performed in step (c). According to one embodiment, at least one washing solution, preferably a washing buffer, is contacted with the particles to which the extracellular nucleic acids are bound. In order to ensure maximum recovery of the bound extracellular nucleic acids, the washing conditions should chosen such that no significant amount of extracellular nucleic acid bound to the nucleic acid binding matrix is removed therefrom during washing.

The washing solution may contain a surfactant. Suitable surfactants include but are not limited to non-ionic surfactants, such as polyoxyethylene-based non-ionic surfactants, preferably selected from the group consisting of polyoxyethylene fatty alcohol ethers, polyoxyethylene alkylphenyl ethers, and polyoxyethylene-polyoxypropylene block copolymers. Preferred examples are TritonX-100 or Brij58, for example at a concentration of about 0.01%-1%.

Washing is particularly recommended, if the isolated extracellular nucleic acids are e.g. supposed to be directly analysed and/or detected e.g. in a diagnostic assay without further purification. If the isolated extracellular nucleic acids are supposed to be directly analysed using methods that are e.g. sensitive to potential impurities (such as e.g. PCR methods), it is recommended to perform at least two washing steps. According to one embodiment, preferably two different volumes of wash solutions are used. Here, the volume of the first washing solution is preferably larger than the volume of the second washing solution. Washing is, however, not necessary if subsequently a detection and/or analysis method is used that is rather insensitive to impurities.

Suitable washing solutions are also known in the prior art (see e.g. WO 2013/045432) and thus, do not need any further description here.

Step (d)—Elution

According to one embodiment, the method further comprises a step (d) of eluting extracellular nucleic acids from the anion exchange particles. This step is optional but preferred.

Any suitable elution method can be used and suitable embodiments are known to the skilled person. Preferably, elution involves changing the pH value. Thus, according to one embodiment, elution occurs at an elution pH which is higher than the binding pH. The choice of the elution pH inter alia depends on the nature of the anion exchange groups present on the particles, the density of the anion exchange groups and the ionic strength of the elution solution(s). The elution pH preferably is at least 0.5 units higher than the binding pH, at least 1 unit higher than the binding pH, more preferably at least 1.5 units higher or at least 2 units higher than the binding pH. The elution pH may be below, at or above the pKa of a protonatable group of the anion exchange group.

Preferably, an elution solution is added to the particles to which the extracellular nucleic acids are bound. The elution may contain a buffering agent but this is not mandatory. It is also within the scope of the present invention to use two or more elution solutions to create the elution conditions. E.g. the two or more elution solutions can be mixed to form a single elution solution that is contacted with the particles or the particles with the bound nucleic acids can be contacted with two or more separate elution solutions that together create when contacted with the particles the elution conditions and hence the "elution solution". The elution preferably occurs at a pH that lies in a range selected from the group consisting of pH 8 and 14; pH 8 and 13.5; pH 8 and 13; 8 and 12.75. Accordingly, an elution solution can be used that has a pH in these ranges. The pH value may also depend on the intended further application of the eluate. If elution occurs at a higher pH value (e.g. 10 or higher), the eluate comprising the nucleic acids can be neutralized e.g. if a respective neutral pH value is beneficial for the intended downstream applications.

Elution can also be assisted by heating and/or shaking. Suitable elution procedures are also described in WO 2013/045432 to which it is referred.

Step (e)—Analyzing the Isolated Extracellular Nucleic Acids

The isolated extracellular nucleic acids can be analysed and/or further processed using suitable assay and/or analytical methods. Hence, according to one embodiment, the isolated extracellular nucleic acids are analysed in a step (e). The analysis can be performed in order to identify, detect, screen for, monitor or exclude a disease, an infection and/or at least one fetal characteristic.

The isolated extracellular nucleic acids and/or a specific target extracellular nucleic acid comprised or suspected of being comprised in the isolated extracellular nucleic acids can be identified, quantified, modified, contacted with at least one enzyme, amplified, reverse transcribed, cloned, sequenced, contacted with a probe and/or be detected. Respective methods are well-known in the prior art and are commonly applied in the medical, diagnostic and/or prognostic field in order to analyse extracellular nucleic acids (see also the detailed description in the background of the present invention). Thus, after extracellular nucleic acids were isolated, optionally as part of total nucleic acid, total RNA and/or total DNA, they can be analysed to identify the presence, absence or severity of a disease state including but not being limited to a multitude of neoplastic diseases, in particular premalignancies and malignancies such as different forms of cancers. E.g. the isolated extracellular nucleic acids can be analysed in order to detect diagnostic and/or prognostic markers (e.g., fetal- or tumor-derived extracellular nucleic acids) in many fields of application, including but not limited to non-invasive prenatal genetic testing respectively screening, disease screening, oncology, cancer screening, early stage cancer screening, cancer therapy monitoring, genetic testing (genotyping), infectious disease testing, pathogen testing, injury diagnostics, trauma diagnostics, transplantation medicine or many other diseases and, hence, are of diagnostic and/or prognostic relevance. According to one embodiment, the isolated extracellular nucleic acids are analyzed to identify and/or characterize a disease infection or a fetal characteristic. The analysis/further processing of the nucleic acids can be performed using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here.

EMBODIMENTS

The method according to the present invention can be performed manually, or by using automated systems. Manual methods can often process larger sample volumes. Automated systems usually have due to their design a certain limit with respect to the volume they can process. Automated systems have in particular the advantage that many samples can be processed at the same time and that automated systems are less error prone, because handling errors are avoided. This is a particular advantage where a high number of samples are to be processed, as is the case in many laboratories were samples are analysed for medical and/or diagnostic purposes. The present method is particularly suitable for automation. Thus, according to one embodiment, the method is performed using an automated system. In this embodiment, it is preferred to use magnetic particles as this simplifies the processing of the particles. The magnetic particles including the bound extracellular nucleic acids can be processed easily by the aid of a magnetic field, e.g. by using a permanent magnet. This embodiment is e.g. compatible with established robotic systems capable of processing magnetic particles. Here, different robotic systems are used in the art that can be used in conjunction with the present method. According to one embodiment, magnetic particles are collected at the bottom or the side of a reaction vessel and the remaining liquid sample is removed from the reaction vessel, leaving behind the collected magnetic particles to which the extracellular nucleic acids are bound. Removal of the remaining sample can occur by decantation or aspiration. Such systems are well known in the prior art and thus need no detailed description here. In an alternative system that is known for processing magnetic particles the magnet which is usually covered by a cover or envelope plunges into the reaction vessel to collect the magnetic particles. The collected particles are then transferred to a new reaction vessel, e.g. in order to perform a washing or elution step. As respective systems are well-known in the prior art and are also commercially available (e.g. QIASYMPHONY®; QIAGEN), they do not need any detailed description here. The automated system QIAsymphony, a commercially available nucleic acid extraction robot capable of fully automated execution of nucleic acid enrichment and purification protocols, was also used in the examples. In a further alternative system for processing magnetic particles, the sample comprising the magnetic silica particles are aspirated into a pipette tip and the magnetic particles are collected in the pipette tip by applying a magnet e.g. to the side of the pipette tip. The remaining sample can then be released from the pipette tip while the collected magnet silica particles which carry the bound target DNA molecules remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

According to one embodiment, the sample volume that is processed with the present method is selected from 0.1 ml to 20 ml, 0.5 ml to 15 ml, 0.75 ml to 10 ml, 1.0 ml to 8 ml, 1.5 ml to 6 ml and 1.75 ml to 5 ml.

Limitations with respect to the sample volume that can be processed at once (as it is e.g. the case with many automated systems) can be overcome by splitting the original sample, processing sample portions in parallel and reunifying e.g. the eluates or the anion exchange material prior to elution. This sample splitting and reunifying of either eluates and/or solid phases allows to easily process larger sample volumes using an automated system which can only process a limited sample volume. In a further highly advantageous embodiment the sample from which extracellular nucleic acids are supposed to be isolated is also split into two or more portions. For the first portion, also referred to as sample portion 1, steps (a) and (b) are performed as described herein. The particles with the bound extracellular nucleic acids obtained from sample portion 1 are then used as particles for the second sample portion (also referred to as sample portion 2), which is otherwise processed according to step (a) as described herein. Thus, the extracellular nucleic acids contained in sample portion 2 bind in step (a) to the same particles to which the extracellular nucleic acids from sample portion 1 were already bound. After the binding step of sample portion 2, particles are provided to which the extracellular nucleic acids from the first and second sample portions were bound. The particles with the bound extracellular nucleic acids from sample portion 1 and sample portion 2 are then separated from the remaining binding mixture of sample portion 2. The bound extracellular nucleic acids from sample portions 1 and 2 can then be optionally washed and eluted as defined in steps (c) and (d) or the particles with the bound extracellular nucleic acids from sample portion 1 and 2 can be used as particles in the binding mixture of a sample portion 3, if existing. This principle can be performed for the number of sample portions present. The bound extracellular nucleic acids from sample portion 1, sample portion 2 and optionally further sample portions, can then be optionally washed and eluted. Thereby, an eluate can be obtained that comprises the extracellular nucleic acids from the original sample. Only one elution step is required. It was found that this principle is particularly advantageous when performing the method using an automated system. Here, the binding mixture for the sample portion 2 can be prepared except for the particles during the time, wherein sample portion 1 is processed and e.g. incubated for binding the extracellular nucleic acids of sample portion 1 to the particles. Furthermore, independent of sample input volume the same amount of particles can be used which is advantageously for a constant/robust elution of nucleic acids.

According to one embodiment, the method comprises
(a) preparing from the biological sample a binding mixture comprising
   i) extracellular nucleic acids;
   ii) magnetic particles providing an anion exchange surface;
   iii) at least one polyoxyethylene fatty alcohol ether in a concentration of 0.1% to 10%, preferably 0.15% to 7.5%, more preferably 0.2% to 6%;
   iv) at least one alkali metal salt;
   (v) optionally at least one proteolytic enzyme;
   wherein the binding mixture has a pH 6.5 so that extracellular nucleic acids bind to the particles,
(b) magnetically separating the magnetic particles with the bound extracellular nucleic acids from the remaining binding mixture;
(c) washing the bound extracellular nucleic acids;
(d) eluting bound extracellular nucleic acids.

Suitable and preferred polyoxyethylene fatty alcohol ethers and anion exchange particles are described above and it is referred to the respective disclosure. The biological sample is according to one embodiment a body fluid or a sample derived from a body fluid such as e.g. plasma or serum. A buffering agent can be used to maintain the pH of the binding mixture.

According to one embodiment, the method comprises
(a) preparing from the biological sample a binding mixture comprising
   i) extracellular nucleic acids;
   ii) magnetic particles providing an anion exchange surface which comprises amine groups;
   iii) at least one polyoxyethylene fatty alcohol ether in a concentration selected from 0.1% to 6%, 0.2% to 5%, 0.25% to 4%, and 0.3% to 3%, wherein the polyoxyethylene fatty alcohol ether is selected from the group consisting of polyoxyethylene cetyl ether, polyoxyethylene stearyl ether and polyoxyethylene oleyl ether and preferably is a polyoxyethylene cetyl ether;
   iv) at least one alkali metal halide, preferably selected from sodium chloride, potassium chloride and lithium chloride, more preferably sodium chloride, in a concentration selected from 100 mM to 1M, 125 mM to 750 mM and 125 mM to 500 mM;
   (v) optionally at least one proteolytic enzyme;
   wherein the binding mixture has a pH 6.5 so that extracellular nucleic acids bind to the particles,
(b) magnetically separating the magnetic particles with the bound extracellular nucleic acids from the remaining binding mixture;
(c) washing the bound extracellular nucleic acids;
(d) eluting bound extracellular nucleic acids.

The biological sample is according to one embodiment a body fluid or a sample derived from a body fluid such as e.g. plasma or serum. A buffering agent can be used to maintain the pH of the binding mixture.

According to one embodiment, the sample from which the extracellular nucleic acids are isolated is a stabilized sample. Many samples such as blood samples or samples derived from blood such as plasma or serum are stabilised upon collection using appropriate stabilizers. E.g. blood or samples derived from blood such as plasma or serum are usually stabilised at least by adding an anticoagulant, preferably a chelating agent such as EDTA or sodium citrate. The used stabilization may add to preserve the extracellular nucleic acid population in the sample. Several methods are known in the prior art that achieve a stabilization of the sample including a stabilization of the extracellular nucleic acid population comprised in the sample. The stabilization prevents the degradation of the extracellular nucleic acids and/or prevents the contamination of the extracellular nucleic acids by intracellular nucleic acids, in particular genomic DNA that is released from cells that are contained in the sample.

Highly efficient stabilization technologies for stabilizing extracellular nucleic acids are described in WO 2013/045457, WO 2013/045458, WO 2014/146781, WO 2014/049022 and PCT/EP2015/055699, herein incorporated by reference. These methods have the advantage that they do not rely on the use of a formaldehyde releaser. The method according to the invention has been shown in experiments to be also highly efficient in isolating extracellular nucleic acids from samples such as blood plasma samples that were stabilized according to these technologies.

A further known principle employs the use of formaldehyde releasers (see e.g. U.S. Pat. Nos. 7,332,277 and 7,442,506). Formaldehyde releaser based stabilization agents are commercially available from Streck Inc. under the name of cell-free RNA BCT (blood collection tube) which are described as being covered by patents U.S. Pat. Nos. 8,304,187 and 8,586,306. Here, the stabilization inter alia involves the use of diazolidinyl urea. However, the use of formaldehyde or formaldehyde-releasing substances has drawbacks, because the isolation of extracellular nucleic acids by induction of crosslinks between nucleic acid molecules or between proteins and nucleic acids can be hampered. Therefore, many conventional nucleic acid isolation methods do not allow the quantitative isolation of extracellular nucleic acids from formaldehyde releaser stabilized samples but result in reduced yields. The method of the invention can be used for effectively isolating extracellular nucleic acids from formaldehyde releaser stabilized samples, such as e.g. plasma samples obtained from blood that was stabilized using a formaldehyde releaser such as diazolidinyl urea. The achievable extracellular nucleic acid yields are high. This is in particular the case, if a proteolytic enzyme is included in the binding mixture.

Therefore, according to one embodiment, the method of the invention is used in order to isolate extracellular nucleic acids from a formaldehyde releaser stabilized sample. Respective stabilization methods that are based on the use of a formaldehyde releaser are known in the prior art and are e.g. disclosed in US 2011/0111410, herein incorporated by reference. The stabilized sample is obtained by contacting the sample, e.g. blood, with at least one formaldehyde releaser. As described herein, cells are preferably removed and the extracellular nucleic acids are isolated from the cell-free fraction of the stabilized sample such as e.g. plasma or serum in case of blood. A formaldehyde releaser is commonly described as a compound which over time releases formaldehyde and/or paraformaldehyde. Suitable "formaldehyde releaser" that can be used in conjunction with the present method include but are not limited to, diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1 aza-3,7-dioxabicyclo[3.3.0] octane, 5-hydroxymethyl-1-1 aza-3,7dioxabicyclo[3.3.0]octane, 5-hydroxypoly[methyleneoxy]methyl-1-1 aza-3,7dioxabicyclo[3.3.0]octane, quaternary adamantine or any combinations of the foregoing. The formaldehyde releaser preferably is a heterocyclic urea and may be selected from the group consisting of diazolidinyl urea (DU), imidazolidinyl urea (IDU), and any combination thereof. In advantageous embodiments, the stabilization involved the use of diazolidinyl urea (DU) and/or imidazolidinyl urea, preferably diazolidinyl urea. The sample may have been contacted with further additives to improve the stabilization effect. For example, when stabilizing blood or a sample derived from blood, the stabilization will involve the addition of an anticoagulant. Examples of anticoagulants that can be comprised in the stabilization composition or can be added separately to the sample include but are not limited to heparin, metal ion chelating agents, in particular citrate, oxalate, EDTA and combinations thereof.

According to one embodiment, total nucleic acids are isolated from the sample and the extracellular nucleic acids are comprised as a portion therein. If the sample is a cell-free or cell-depleted sample, the total nucleic acids isolated therefrom will predominantly comprise or even consist of extracellular nucleic acids. It is also within the scope of the present invention to isolate at least predominantly a specific target nucleic acid. A target nucleic acid can be e.g. a certain type of nucleic acid, e.g. RNA or DNA, including mRNA, microRNA, other non-coding nucleic acids, epigenetically modified nucleic acids, and other nucleic acids that are contained in the extracellular nucleic acid population. It is also within the scope of the present invention to e.g. digest the non-target nucleic acid using nucleases after isolation. The term target nucleic acid can also refer to a specific kind of nucleic acid, e.g. an extracellular nucleic acid that is known to be a certain disease marker or a viral nucleic acid. As discussed above, the isolation of extracellular nucleic acids may also comprise the specific isolation of a respective target nucleic acid e.g. by using appropriate capture probes. The term "a target nucleic acid" also refers to a nucleic acid having a certain length, e.g. a nucleic acid having a length of 2000 nt or less, 1000 nt or less or 500 nt or less (as discussed above, the chain length indicated by "nt" refers to bp in case of double-stranded DNA). Isolating respective smaller target nucleic acids can be advantageous because it is known that extracellular nucleic acids usually have a smaller size of less than 2000 nt, usually less than 1000 nt and often even less than 500 nt. Focusing the isolation, respectively purification, on respective small nucleic acids can increase the portion of extracellular nucleic acids obtained in the isolated nucleic acids.

Preferably, the kit according to the second aspect is used in order to perform the method according to the first aspect. Regarding the characteristics of the kit, it is referred to the subsequent disclosure.

Kit

According to a second aspect, a kit for performing the method according to the first aspect is provided. Said kit comprises
(a) a lysis and/or binding composition comprising
   i) at least one polyoxyalkylene fatty alcohol ether;
   ii) at least one salt;
   iii) at least one buffer;
   wherein said composition has an acidic pH;
(b) particles providing an anion exchange surface; and
(c) optionally a proteolytic enzyme;
(d) optionally one or more wash solutions and
(e) optionally one or more elution solutions.

The kit can be used in order to perform the method according to the first aspect. The advantages were described above. Including a polyoxyalkylene fatty alcohol ether in the lysis and/or binding composition that is added to the sample to prepare the binding mixture is advantageous. Variations in the anion exchange surface that can occur during storage of the particles are compensated, thereby improving the isolation results. The isolated nucleic acids are of high quality and purity. The method thereby becomes more reliable which is an important advantage in particular when extracellular nucleic acids are isolated for the medical and/or diagnostic field.

The lysis and/or binding composition comprises at least one polyoxyalkylene fatty alcohol ether. Details were described above and it is referred to the above disclosure which also applies here. As discussed above, the polyoxyalkylene fatty alcohol ether can be selected from polyoxyethylene cetyl, polyoxyethylene oleyl and polyoxyethylene stearyl alcohol ethers and is preferably selected from the group consisting of polyoxyethylene(10) cetyl ether (Brij® 56), polyoxyethylene(20) cetyl ether (Brij® 58), polyoxyethylene(20) stearyl ether (Brij® 78) and polyoxyethylene (20) oleyl ether (Brij® 98). The use of a polyoxyethylene (20) cetyl ether is particularly preferred.

The at least one polyoxyalkylene fatty alcohol ether, which preferably is a polyoxyethylene fatty alcohol ether, may be comprised in the lysis and/or binding composition in a concentration of 0.2% up to the saturation limit. Suitable concentrations include but are not limited to 0.5% to 15%, 0.75% to 12.5%, 1% to 10%, 1.5% to 7.5% and 2% to 6%. In case more than one polyoxyalkylene fatty alcohol ether is comprised in the lysis and/or binding composition, the indicated concentration ranges refer according to one embodiment to the total concentration of comprised polyoxyalkylene fatty alcohol ethers.

The lysis and/or binding composition comprises a salt. The salt is according to one embodiment an alkali metal salt or an ammonium salt. The alkali metal salt is preferably an alkali metal halide. Suitable examples include sodium chloride, potassium chloride and lithium chloride, wherein sodium and potassium chloride being preferred. According to one embodiment, sodium chloride is used. The salt may be comprised in the lysis and/or binding composition in a concentration selected from 100 mM to 4M, 200 mM to 3.5M, 300 mM to 3M, 500 mM to 2.5M, 750 mM to 2.25M and 1M to 2M.

The lysis and/or binding composition comprises a buffer. The buffer is preferably acidic. Suitable buffers were described above in conjunction with the method. They include but are not limited to acidic buffering agents such as carboxylic acids, e.g. acetic acid, sodium acetate/acetic acid buffers, citric acid/citrate buffers, maleic acid, malonic acid and tartaric acid, phosphoric acid based buffers, phosphate buffers and amino acid based buffers such as glycine, glutamate/glutamine, aspartate/asparagine. The use of carboxylic acids such as citric acid is preferred.

The lysis and/or binding composition has an acidic pH. The pH of the composition can lie in a range selected from 3 to 6.5, 3.5 to 6 and 4 to 5.5. When contacting the sample with the lysis and/or binding composition, the pH of the sample is lowered and the binding pH is established.

The kit furthermore comprises particles providing an anion exchange surface. Details regarding the particles and the anion exchange groups were described in detail above and it is referred to the above disclosure which also applies here. Preferably, the particles comprise amino groups, such as e.g. primary, secondary or tertiary amino groups. As discussed above, the particles are preferably magnetic.

The kit may furthermore comprise a proteolytic enzyme. Details were described above and it is referred to the above disclosure which also applies here. Preferably, the proteolytic enzyme is proteinase K. The enzyme is preferably not included in the lysis and/or binding composition.

The kit may furthermore comprise one more washing solutions. Details were described above and it is referred to the above disclosure which also applies here.

The kit may also comprise one or more elution solutions. Details were described above and it is referred to the above disclosure which also applies here.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification, the singular forms "a", "an" and "the" include plural aspects unless the context clearly dictates otherwise. Thus, for example, reference to "a polyoxyalkylene fatty alcohol ether" includes a single type of polyoxyalkylene fatty alcohol ether, as well as two or more polyoxyalkylene fatty alcohol ether. Likewise, reference to "a" "salt", "additive", "buffer" and the like includes single entities and combinations of two or more of such entities. Reference to "the disclosure" and "the invention" and the like includes single or multiple aspects taught herein; and so forth. Aspects taught herein are encompassed by the term "invention".

The term "solution" as used herein in particular refers to a liquid composition, preferably an aqueous composition. It may be a homogenous mixture of only one phase but it is also within the scope of the present invention that a solution comprises solid additives such as e.g. precipitates, in particular of contained chemicals such as stabilizing agents.

The sizes, respectively size ranges indicated herein with reference to nucleotides (nt), refer to the chain length and thus are used in order to describe the length of single-stranded as well as double-stranded molecules. In double-stranded molecules said nucleotides are paired.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

The present application claims priority of EP 15171466 (filed: Jun. 10, 2015), the disclosure of which is herewith incorporated by reference.

EXAMPLES

Materials and Methods

Plasma samples were obtained from whole blood samples by performing two centrifugation steps to remove cells (15 min at 1.900×g, 10 min (4° C.) at 16.000×g). Extracellular DNA (ccfDNA) were isolated from plasma samples (2 ml if not indicated otherwise) using an automated system (QIAsymphony). The plasma was contacted with the following reagents to prepare the binding mixture (pH approx. 5):

A lysis/binding buffer (pH 4-5) comprising an alkali metal salt (1.5 to 2M), a carboxylic acid and a non-ionic detergent. In the performed experiments, different non-ionic detergents were used and compared in different concentrations (see below). The lysis/binding buffer supports the digestion of the sample and the release of the extracellular nucleic acids. It establishes the binding conditions.

Proteinase K to digest proteins contained in the sample.

Magnetic silica particles comprising tertiary amine groups as anion exchange groups (approx. 3 mg for 2 ml plasma).

The binding mixture was incubated for 20 min to allow binding of ccfDNA to the anion exchange particles. The bound ccfDNA was washed three times and eluted using 75 µl of an alkaline elution solution (pH approx. 12).

For comparison, ccfDNA was isolated from plasma with the QIAamp circulating nucleic acid kit (QIAGEN GmbH), using the protocol for "purification of circulating nucleic acids from 1 ml, 2 ml, or 3 ml serum or plasma". If not stated otherwise, 2 ml of plasma was mixed with proteinase K and lysis buffer ACL, incubated for 30 min at 60° C., mixed with buffer ACB, bound on QIAamp Mini columns (which comprise a silica solid phase for binding the nucleic acids) with the use of a QIAvac 24 Plus vacuum manifold, washed and eluted with 60 µl and 75 µl elution buffer AVE, respectively, according to the manufactures recommendations.

The nucleic acid yield (18s rDNA (66 bp) and 18s rDNA (500 bp) obtained was analyzed by PCR and compared to a genomic DNA dilution series to determine the copy number. The isolated ccfDNA was analyzed in a real time PCR assay on Abi Prism HT7900 (Life technologies) using 8 µl of eluate if not stated otherwise. In a 20 µl assay volume using QuantiTect Multiplex PCR Kit reagents (QIAGEN GmbH) two fragments of the human 18S rDNA gene, 66 bp and 500 bp, were amplified in a multiplex PCR. Cycle thresholds (Ct values) of the individual samples were translated into amount of gDNA in the eluate according to a gDNA standard curve: total quantification was achieved by comparison with a standard curve generated with human genomic DNA diluted from 10.000 to 10 genome equivalents (1 genome equivalent equates to around 3.6 µg of human genomic haploid DNA). Thereby, the copy number in the eluate can be determined. This copy number was then divided by the amount of eluate used (e.g. 8 in case 8 µl eluate was used) in order to eliminate differences in the amount of eluate used. Thereby, the copy number per µl eluate is determined. This value was then multiplied by the amount of total eluate, e.g. 75 in case the eluate volume was 75 µl. Thereby, the copy number in the eluate is determined and can be compared between different experiments. In addition, this calculated total copy number was then divided by the amount of plasma volume used (e.g. 2 in case 2 ml plasma was used) in order to eliminate differences in the amount of plasma volume used. Thereby, the copy number per ml plasma is determined and can be compared between different experiments.

particles and therefore, achieves that ccfDNA is isolated consistently with high yield even when being confronted with variations in the anion exchange surface. This advantageous effect was not seen when using Triton X-100 as non-ionic detergent.

In example 1, four different bead lots of the same type of anion exchange particles were used. These bead lots were known from previous experiments to show a reduced ccfDNA recovery when Triton X-100 was used as non-ionic detergent in the binding mixture. In contrast, when using the polyoxyethylene fatty alcohol ether Brij58 in the binding mixture, a considerably more robust performance with regard to ccfDNA recovery was seen (see FIG. 1). Analysis of the binding mixture remainders from which the particles with the bound ccfDNA was removed (supernatant) confirmed that the reduced ccfDNA yield using Triton X-100 is

TABLE 1 summarizes the information of the used DNA target sequences detected by quantitative real time PCR

| Target description | position | Sequence position | 5' - 3' | dye |
|---|---|---|---|---|
| h185 rDNA 66 bp amplicon | p12 - region of chromosome 13, 14, 15, 21, 22 | Forward (SEQ ID NO. 1) reverse (SEQ ID NO. 2) probe (SEQ ID NO. 3) | GCCGCTAGAGGTGAAAT TCTTG<br><br>CATTCTTGGCAAATGCT TTCG<br><br>ACCGGCGCAAGACGGAC CAGA | 5' Bodipy - BHQ 3' |
| h185 rDNA 500 bp amplicon | p12 - region of chromosome 13, 14, 15, 21, 22 | forward (SEQ ID NO. 4) reverse (SEQ ID NO. 5) probe (SEQ ID NO. 6) | GTCGCTCGCTCCTCTCCT ACTT<br><br>GGCTGCTGGCACCAGACT T<br><br>CTAATACATGCCGACGGG CGCTGAC | 5' FAM- BHQ 3' |

Example 1

It was found that small differences in the anion exchange surface of the particles (most likely available positively-charged groups) results in large effects on ccfDNA recovery although saturation of beads with ccfDNA is not limiting due to very low concentration of ccfDNA in plasma. One explanation is that impurities (available in huge excess in plasma) compete with ccfDNA for binding to the anion exchange particles. In addition, affinity of ccfDNA strongly depends on its available negatively-charged backbone which in turn depends on its release from interacting proteins. Therefore small changes in anion exchange surface may strongly affect competing affinity of impurities and ccfDNA resulting in significant reduction of ccfDNA recovery. Such changes in the anion exchange surface may occur during the manufacturing process of the anion exchange particles or during prolonged storage of the particles, e.g. when being provided as kit. This effect is seen when using no detergent in the binding mixture and was also seen when using the non-ionic detergent Triton X-100 in the binding mixture.

Example 1 demonstrates that including a polyoxyalkylene fatty alcohol ether such as Brij58 in binding buffer compensates differences in anion exchange particle performance. The results indicate that the polyoxyethylene fatty alcohol ether increases the affinity of ccfDNA to the anion exchange based on a high fraction of ccfDNA that is found in the supernatants and which accordingly was not bound to anion exchange particles during the binding step even though the anion exchange surface is in large excess to the ccfDNA present in the sample.

Example 2

Figure 2:
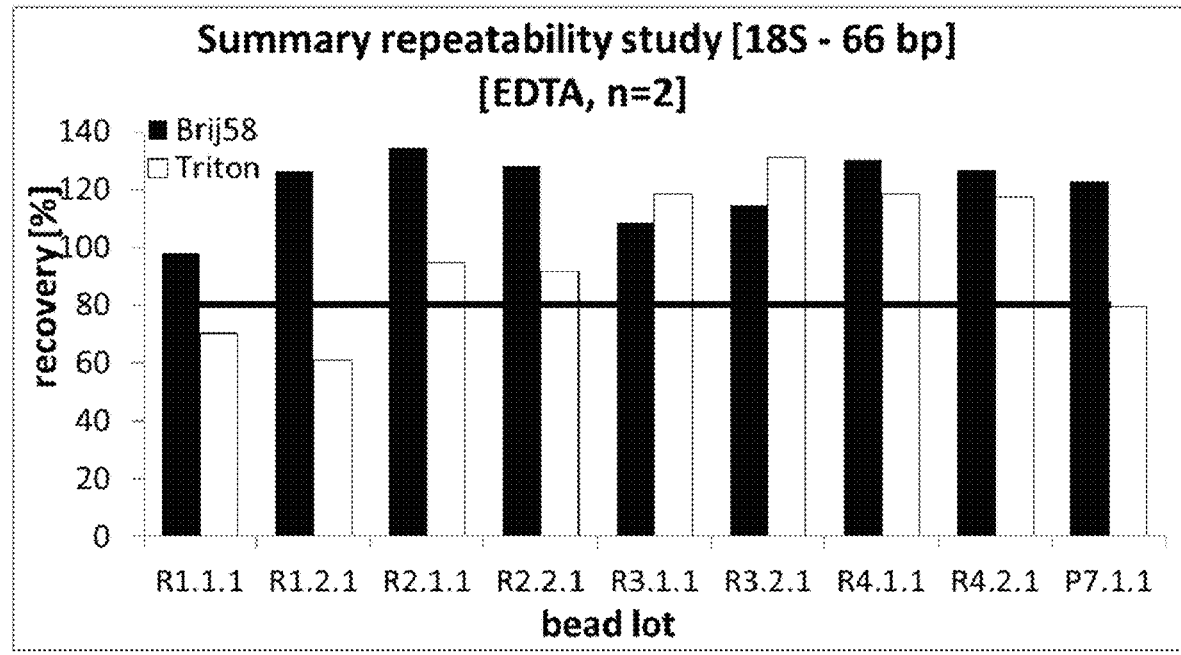
FIG. 2: ccfDNA from 2 ml plasma was extracted using (I) an automated extraction protocol for isolating circulating DNA using magnetic anion exchange particles (comparing different bead lots with Triton X-100 and Brij58 in the binding buffer) and as a reference method (II) the QIAamp Circulating NA Kit. The plasma samples were obtained from blood samples that were stabilized using EDTA. Eluates were subjected to real-time PCR (18S coding sequence; duplex PCR: 66 bp amplicon shown) and ccfDNA recovery was calculated as copies per ml plasma and compared to the manual QIAamp Circulating NA kit (recovery set to 100%). Including a polyoxyethylene fatty alcohol ether, here Brij58, in the binding buffer and hence binding mixture results in more robust ccfDNA recovery using susceptible bead lots compared to Triton X-100.

The increased robustness for ccfDNA recovery using more susceptible beads ("ageing process") in combination with binding conditions that incorporate Brij58 in the binding mixture was confirmed in a second experimental setup where extracellular nucleic acids were isolated from EDTA stabilized blood plasma. For anion exchange particles showing a decreased performance within two months of storage (R1.1.1 and R1.2.1) or reference beads showing a reduced performance after 7 months of storage (P7.1.1) ccfDNA yield could be restored to the initial yields if Brij58 was used as non-ionic detergent in the binding mixture (see FIG. 2). Anion exchange particles showing a good performance with regards to ccfDNA recovery with Triton X-100 could not be further increased in performance if Brij58 was used.

Example 3

Different further detergents were tested to evaluate their impact on ccfDNA recovery. Detergents such as CTAB, DTAB, CHAPS showed a poor performance compared to Triton X-100 (data not shown).

Example 4

Figure 3:
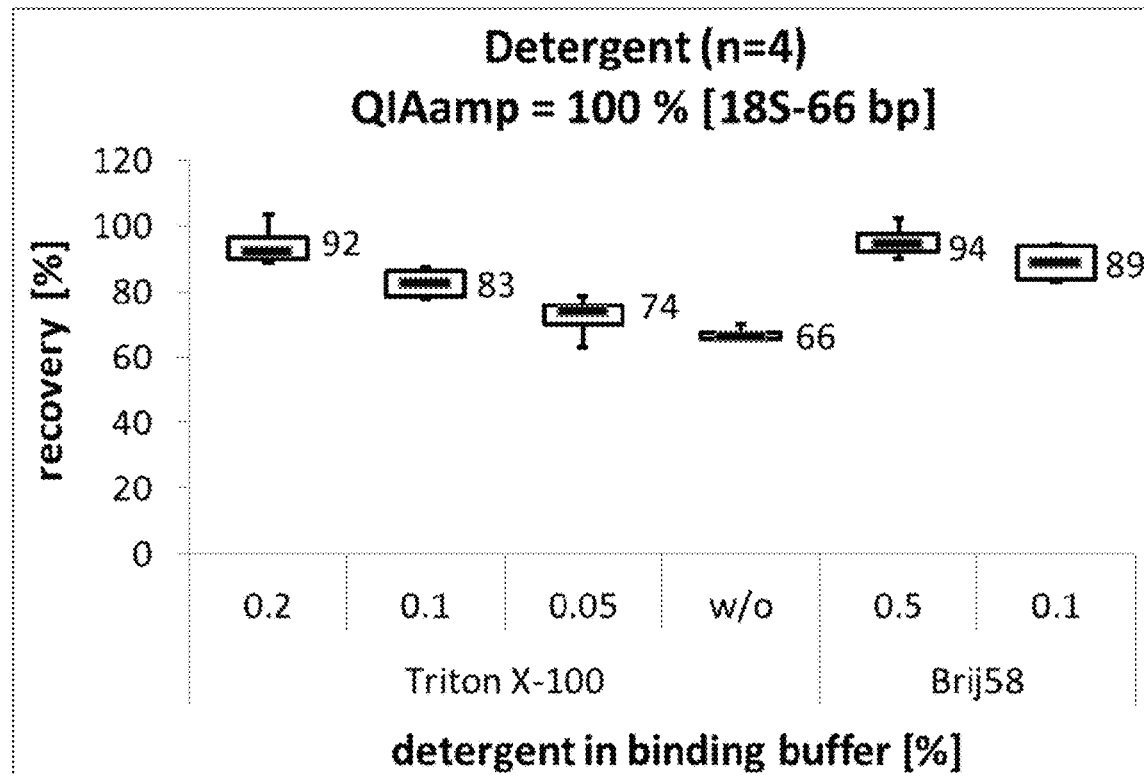
FIGS. 3 to 5: ccfDNA from 2 ml plasma was extracted using (I) an automated extraction protocol for isolating circulating DNA using magnetic anion exchange particles (comparing different detergent concentrations for Triton X-100 and Brij58 in the binding buffer) and as a reference method (II) the QIAamp Circulating NA Kit. Eluates were subjected to real-time PCR (18S coding sequence; duplex PCR: 66 bp or 500 bp amplicon shown) and ccfDNA recovery was calculated as copies per ml plasma and compared to the manual QIAamp Circulating NA kit (recovery set to 100%). The results show that a polyoxyethylene fatty alcohol ether, here Brij58, in the binding buffer and hence binding mixture results in comparable or higher ccfDNA yield to Triton X-100 and can be used in various concentrations in the binding mixture.
Figure 4:
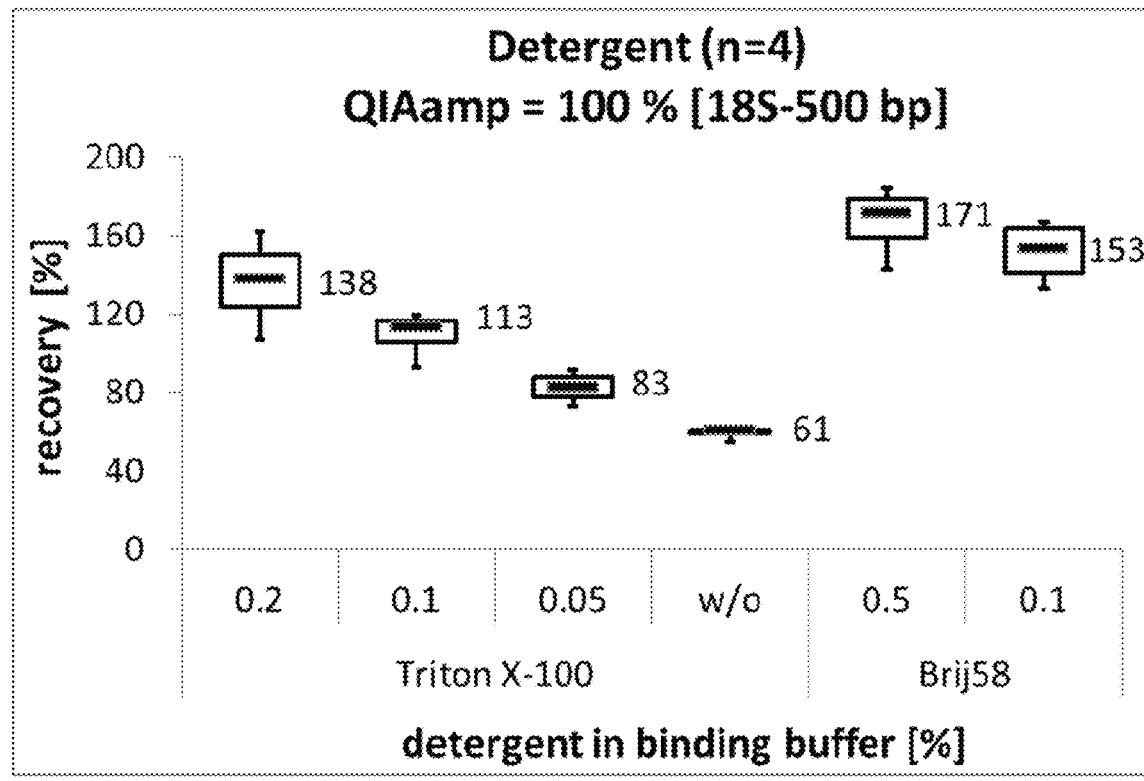

Experiments were performed to compare different concentrations of the non-ionic detergents Triton X-100 and Brij58 (a polyoxyethylene fatty alcohol ether) in the binding mixture. The aim was to evaluate the influence of the non-ionic detergent on ccfDNA extraction efficiency. FIG. 3 illustrates that Brij58 showed comparable ccfDNA recovery compared to Triton X-100 for amplification of the small amplicon (66 bp) in real-time PCR (18S coding sequence). Amplification of the 500 bp amplicon revealed an improved extraction efficiency/purity for large DNA fragments using 0.5% Brij58 in the binding mixture compared to 0.2% Triton X-100 (see FIG. 4).

Figure 5:
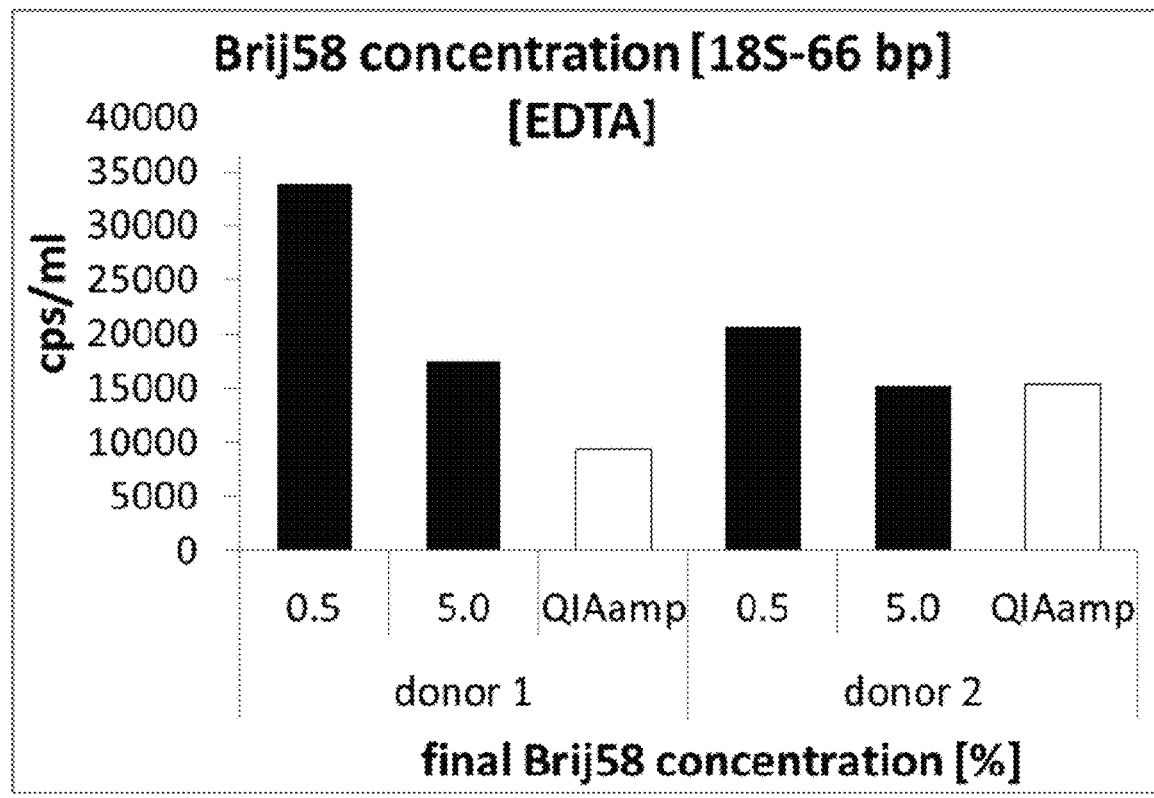

Further experiments comparing different concentrations of Brij58 in binding buffer showed no significant difference in ccfDNA extraction performance in a range of 0.1-2.0% Brij58 in binding mixture. As is shown in FIG. 5, also higher concentrations up to 5% Brij 58 in the binding mixture could be used while achieving a comparable performance as the reference (QIAamp circulating nucleic acid kit). Therefore, the polyoxyalkylene fatty alcohol ether Brij58 was effective in various concentrations in the binding mixture. Furthermore, the polyoxyalkylene fatty alcohol ether showed a higher solubility in the lysis and/or binding composition compared to Triton X-100. Therefore, Brij58 could also be used in higher concentrations in the lysis and/or binding composition as well as in the binding mixture. Increased concentrations of Triton X-100 as well as storage of lysis and/or binding composition containing Triton X-100 at 45° C. (simulating long term storage) exceeds the limit of solubility for Triton X-100. This effect was not seen with Brij58 in the experiments.

Example 5

It was analyzed whether the improvement seen with the eluates that were obtained using the protocol wherein Brij58 was included in the binding mixture was attributable to an increase in ccfDNA yield and/or was attributable to a higher purity of the eluate. Purer eluates show less inhibitory effects on the PCR reaction because the eluates comprises less or is even free of PCR inhibitors. This in turn increases detection of ccfDNA and thus improves the results.

Figure 6:
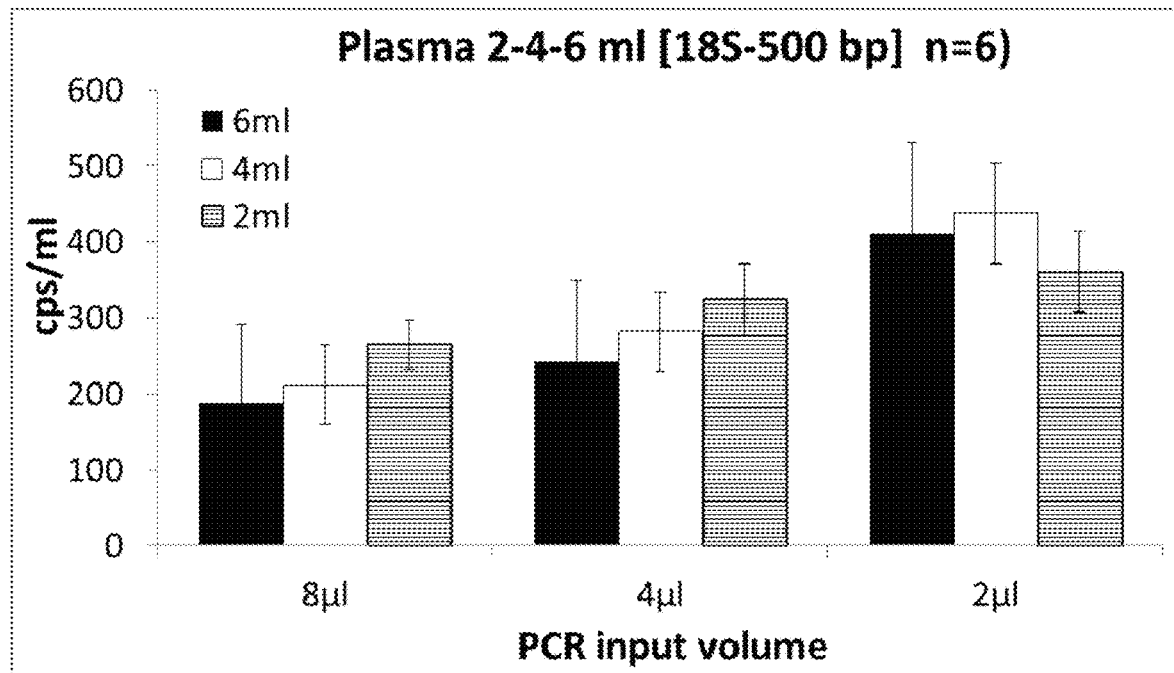
FIGS. 6 and 7: ccfDNA from 2, 4 and 6 ml plasma obtained from blood stabilized with Cell-free DNA BCT (Streck Inc, Cat. No: 218962) was extracted with an automated extraction protocol for isolating circulating DNA using magnetic anion exchange particles t using either Triton X-100 (FIG. 6) or Brij58 (FIG. 7) in the binding mixture. Eluates were subjected to real-time PCR (18S coding sequence; duplex PCR: 500 bp amplicon shown) using different eluate input volumes (2-8 µl; Σ20 µl). ccfDNA recovery was calculated as copies per ml plasma. Including a polyoxyethylene fatty alcohol ether, here Brij58, in the binding mixture results in more efficient removal of impurities compared to Triton X-100.
Figure 7:
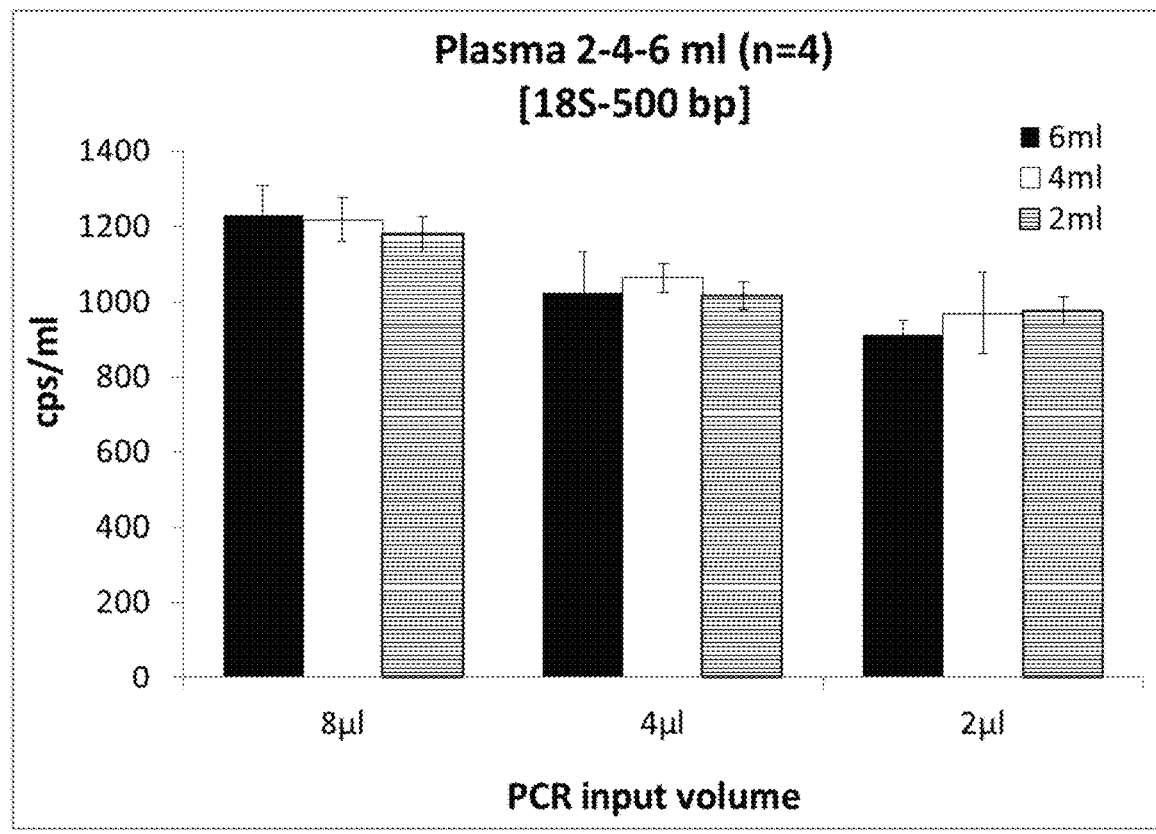

FIGS. 6 and 7 show the influence of Brij58 in the binding mixture on the purity of the eluates and the subsequent PCR efficiency/PCR inhibition compared to Triton X-100. When Triton X-100 was used in the binding mixture (see FIG. 6), PCR inhibition was seen to some extent and a reduced ccfDNA yield for the large 500 bp amplicon was shown if the plasma input volume is increased from 2 to 6 ml (increased concentration of impurities in eluate) and increased input volume from 2 to 8 µl is used in the PCR.

In contrast, no PCR inhibition was seen when using Brij58 in the binding mixture (see FIG. 7). A comparable ccfDNA yield was found for the large 500 bp amplicon for 2 to 6 ml plasma input volume and slightly increased ccfDNA recovery if an increased input volume from 2 to 8 µl is used in the PCR.

One explanation for the clearly increased purity of eluates accompanied with an increased compatibility to downstream applications is the critical micelle concentration (CMC). Triton X-100 is used in a final concentration of 1.6 mM (CMC: 0.2-0.9 mM) and Brij58 is used in a final concentration of 4.5 mM (CMC: 0.08 mM). Most likely Brij58 forms micelles within the processing solution which may include impurities from plasma thereby preventing binding of impurities to beads.

Removing of impurities may not only affect purity of eluates but may also affect affinity of ccfDNA to AnEx beads due to (I) reduced availability of competitor impurities (embedded in micelles) and (II) more "naked" ccfDNA (removal of impurities (=proteins) from DNA-protein complexes) which shows a higher affinity to AnEx beads compared to DNA enclosed in protein complexes.

Example 6

It was surprisingly found that the temperature during digestion influences the ccfDNA yield. In Example 6, ccfDNA was extracted from 2 ml plasma sample. The digestion conditions were modified by using either 30 µl or 60 µl ProtK in the binding mixture in combination with incubation for 10 min at room temperature or at 65° C. The magnetic anion exchange particles were added to bind the ccfDNA after the sample was digested in the presence of ProtK in the binding buffer. Each condition was tested in 6 replicates.

Figure 8:
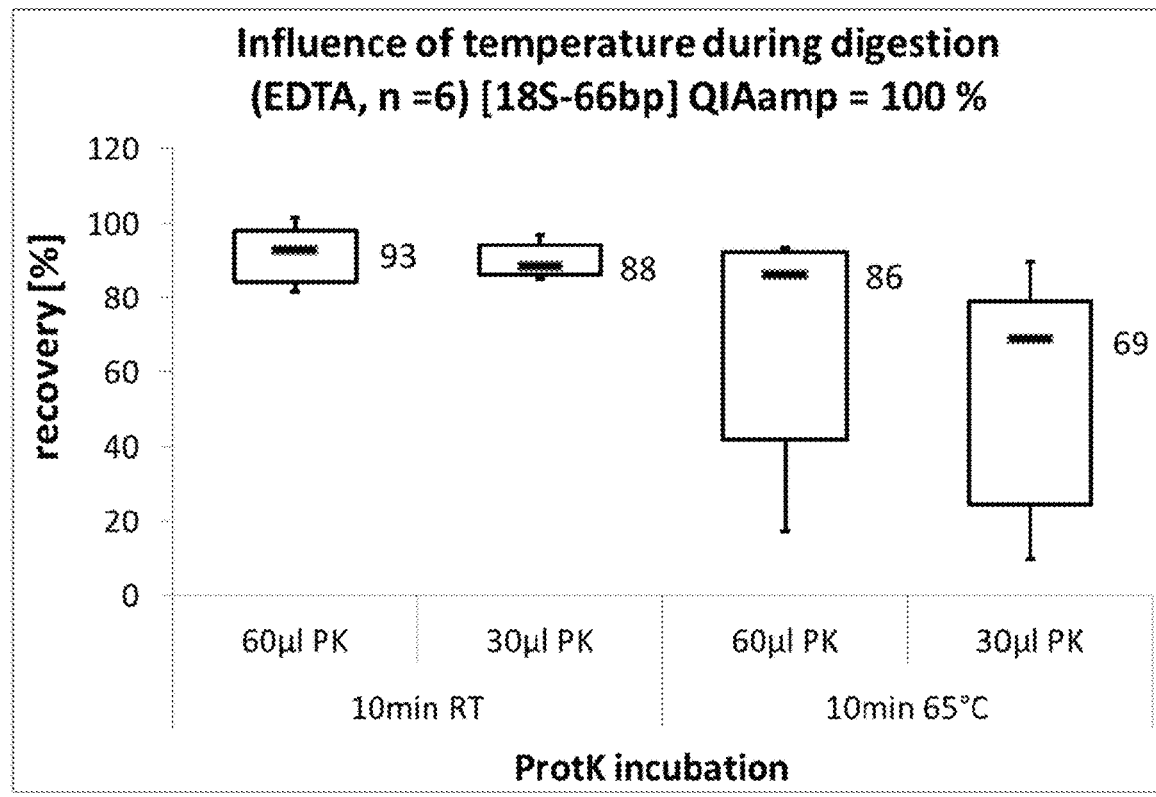
FIG. 8: Elevated temperatures during lysis involving proteinase K results in decreased ccfDNA yield. ccfDNA from 2 ml plasma was extracted using (I) an automated extraction protocol for isolating circulating DNA using magnetic anion exchange particles. Digestion was performed using 30 µl or 60 µl ProtK in the binding mixture in combination with incubation for 10 min at room temperature or at 65° C. As reference method (II) the QIAamp Circulating NA Kit was used. Eluates were subjected to real-time PCR (18S coding sequence; duplex PCR: 66 bp amplicon shown) and ccfDNA recovery was calculated as copies per ml plasma and compared to the manual QIAamp Circulating NA kit (recovery set to 100%).

It was surprisingly found that elevated temperatures during lysis decreased the ccfDNA yield. 2 of the 6 replicates showed a strong decrease in the ccfDNA yield when either 30 µl or 60 µl ProtK was used at 65° C. In contrast, the samples processed at room temperature consistently provided good yields and no drop outs were encountered. FIG. 8 summarizes the results in form of a box-plot. As can be seen, at the elevated temperature a broad box is obtained (25-75% recovery). Therefore, it is advantageous to perform the digestion at room temperature to increase the uniformity and reliability of the extraction result and hence to ensure consistent, high ccfDNA yields.

Example 7

Further experiments were performed to compare the results achieved with other polyoxyalkylene fatty alcohol ether non-ionic detergents with the results achieved with the polyoxyalkylene fatty alcohol ether Brij58. The following non-ionic detergents were tested using the automated extraction protocol for isolating circulating DNA from plasma samples using magnetic anion exchange particles described above:

Brij 58 (a polyoxyethylene cetyl ether);
Brij 35 (a polyoxyethylene lauryl ether);
Brij 78 (a polyoxyethylene stearyl ether); and
Brij 98 (a polyoxyethylene oleyl ether).

The plasma samples were obtained from blood samples that were stabilized using the product Cell-free DNA BCT (Streck Inc, Cat. No: 218962). 2 ml plasma was contacted with 300 µl binding buffer, the different detergents, proteinase K and the magnetic anion exchange particles which carried tertiary amine groups as anion exchange groups. Each non-ionic detergent was tested in a final concentration in the binding mixture of 2%, 0.5% and 0.1%. Each condition was tested in 2 replicates (n=2). The binding mixture was incubated approx. 20 min to allow binding of the ccfDNA to the anion exchange particles. The magnetic particles with the bound ccfDNA was separated from the remaining sample, washed three times and eluted using 75 µl of an alkaline elution solution (pH approx. 12.0) (see also above, Materials and methods).

Eluates were subjected to real-time PCR (18 S coding sequence; duplex PCR) and ccfDNA recovery was calculated as copies per ml plasma. The results obtained with the different non-ionic polyoxyethylene fatty alcohol ether detergents in the binding mixture were compared to the results obtained with Brij 58 in equal concentrations (Brij 58 ccfDNA recovery at 2% set to 100%).

Figure 9:
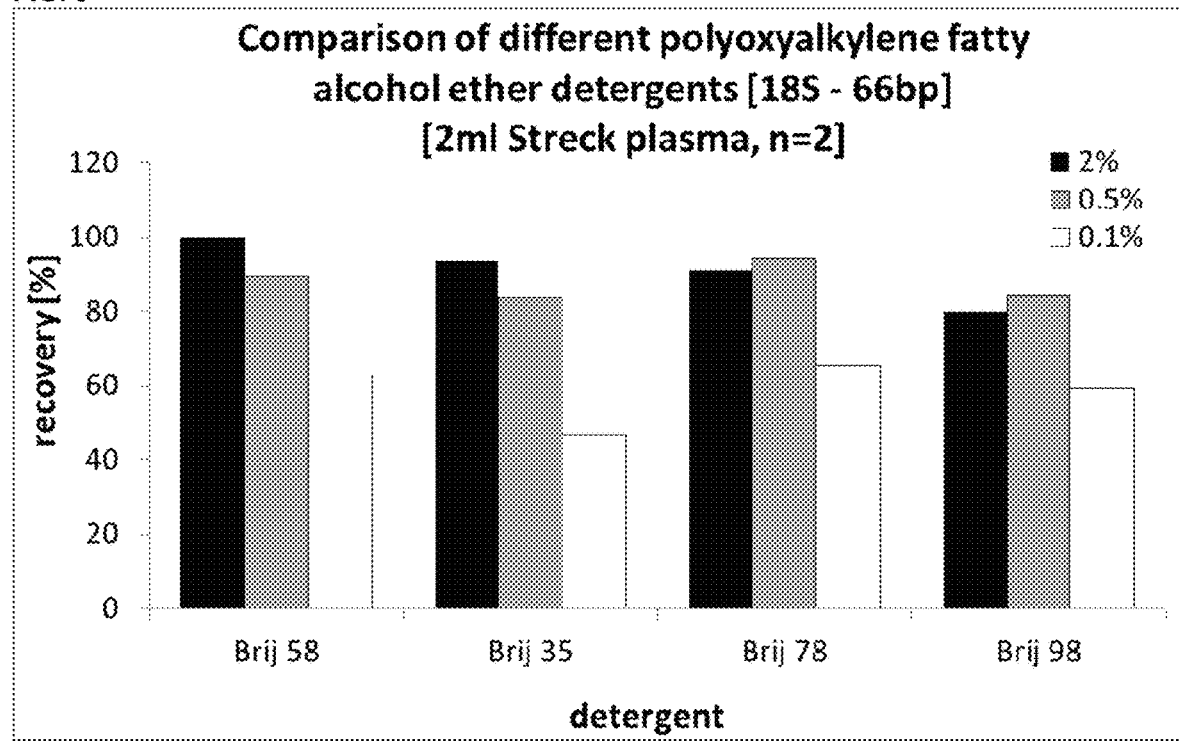
FIG. 9: ccfDNA from 2 ml plasma was extracted using an automated extraction protocol for isolating circulating DNA using magnetic anion exchange particles. Different polyoxyethylene fatty alcohol ether non-ionic detergents were used in different concentrations in the binding mixture (2.0%, 0.5% and 0.1%). Eluates were subjected to real-time PCR (18S coding sequence; duplex PCR: 66 bp amplicon shown). The results show that different polyoxyethylene fatty alcohol ethers achieve advantageous results similar to Brij58.

The results are shown in FIG. 9 (66 bp amplicon shown). As can be seen, also the other tested polyoxyalkylene fatty alcohol ether non-ionic detergents showed good results similar to Brij58. This demonstrates that the advantageous effects shown in the previous examples are not limited to Brij58 but are also achieved with other polyoxyalkylene fatty alcohol ethers.

Example 8

The influence of increased plasma volume (increasing the risk of PCR inhibition) on the results was analysed using either 2 ml or 4 ml plasma volume and different non-ionic detergents in the binding mixture. The following non-ionic detergents were tested (final concentration in the binding mixture 0.5% for each non-ionic detergent tested):
1. Polyoxyalkylene fatty alcohol ethers
   Brij 58 (set as reference to 100% ccfDNA recovery);
   Brij 35;
   Brij 78;
   Brij 98.
2. Other non-ionic detergents
   Triton X-100;
   Igepal CA630;
   Igepal C0630.

In one set-up, no detergent was included in the binding mixture. Each condition was tested in 2 replicates (n=2).

ccfDNA was extracted from 2 ml plasma (Streck) using the protocol described in Example 7. For extracting ccfDNA from 4 ml plasma, the following protocol was used: Two 2 ml plasma aliquots were obtained from each plasma sample. A first binding mixture was prepared as described in Example 7 from a first 2 ml plasma aliquot and the ccfDNA was bound to the magnetic anion exchange particles. The magnetic particles with the bound ccfDNA were then transferred as anion exchange particles into a second binding mixture (not yet containing anion exchange particles) that was prepared from the second 2 ml plasma aliquot. The binding mixture was again incubated to bind the ccfDNA from said second binding mixture to the anion exchange particles to which the ccfDNA from the first binding mixture were already bound. After this second binding step, ccfDNA from overall 4 ml plasma is bound to the anion exchange particles. Washing and elution was then performed as described in Example 7.

Eluates were subjected to real-time PCR (18 S coding sequence; duplex PCR) and ccfDNA recovery was calculated as copies per ml plasma so that the results for the 2 ml plasma samples are comparable to the results of the 4 ml plasma sample.

Figure 10:
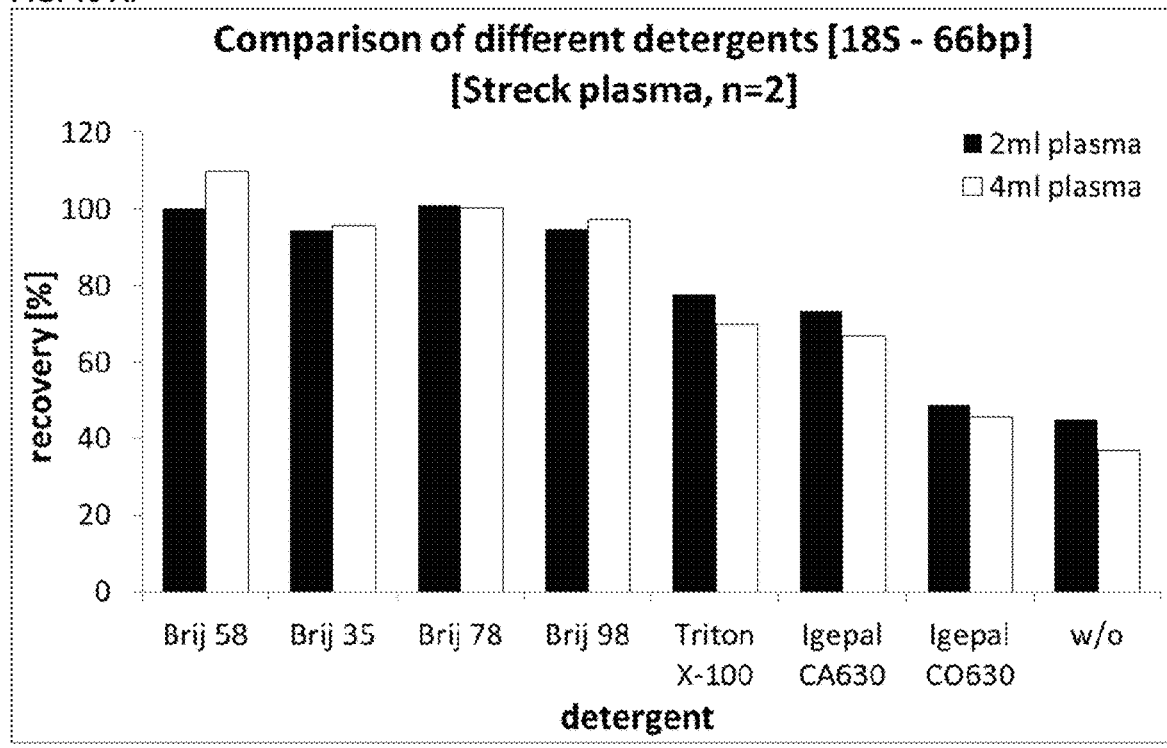
FIGS. 10A-10B: ccfDNA from 2 ml and 4 ml plasma was extracted using an automated extraction protocol for isolating circulating DNA using magnetic anion exchange particles and different non-ionic detergents in the binding mixture. Eluates were subjected to real-time PCR (18S coding sequence; duplex PCR: 66 bp (FIG. 10 A.) or 500 bp amplicon (FIG. 10 B.) shown). The results show that the use of polyoxyethylene fatty alcohol ethers in the binding mixture provides superior results compared to other non-ionic detergents with respect to yield and purity.
Figure 10:
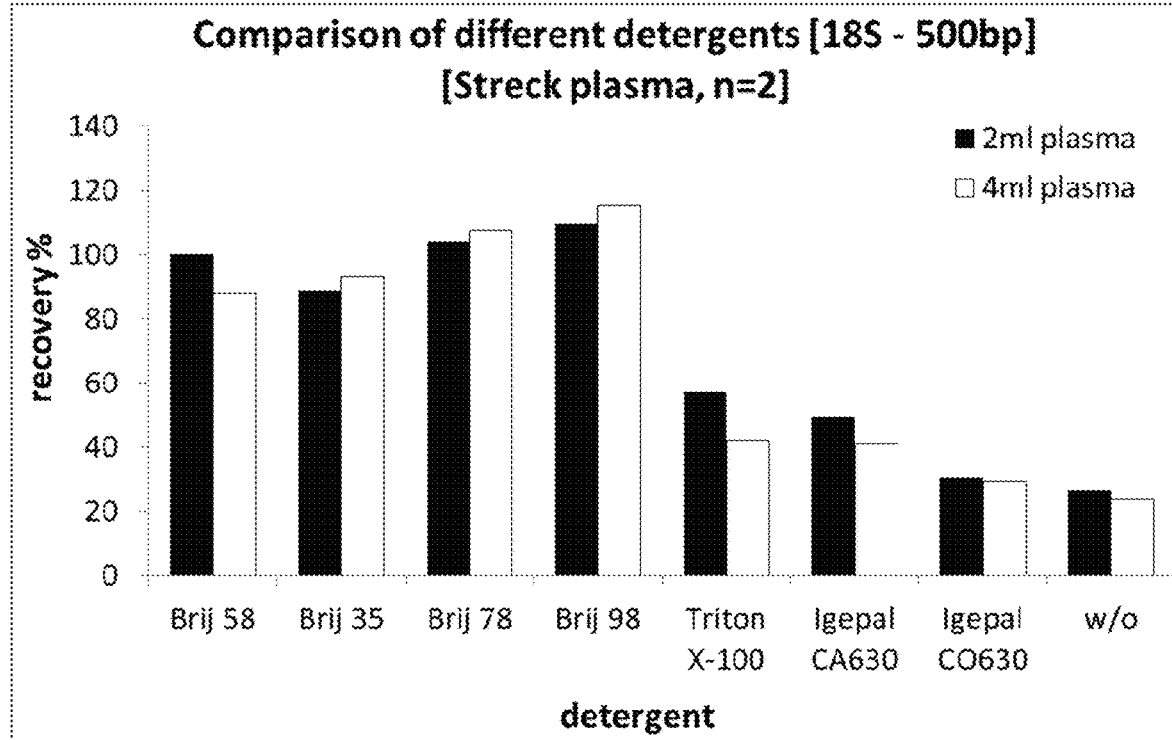

The results are shown in FIG. 10 A (66 bp amplicon) and FIG. 10 B (500 bp amplicon). As can be seen, the non-ionic detergents that are used according to the invention (polyoxyalkylene fatty alcohol ether) recovered ccfDNA with high yields and showed a stable performance irrespective of whether 2 ml or 4 ml plasma was processed. No increased PCR inhibition was seen. For the other non-ionic detergents tested in comparison, the overall ccfDNA yield was reduced compared to the results obtained with the polyoxyalkylene fatty alcohol ethers. Moreover, the calculated ccfDNA recovery per ml was less when processing 4 ml plasma. This is an indicator that PCR inhibitors were carried over during the purification, thereby rendering less pure eluates. Such inhibitory effect is more pronounced in the 500 bp amplicon, because the longer fragment is more susceptible to PCR inhibition. The differences between the tested polyoxyethylene fatty alcohol ethers compared to the other tested non-ionic detergents is even more pronounced when looking at the 500 bp fragment, thus indicating PCR inhibition. This can be avoided when using a polyoxyethylene fatty alcohol ether as non-ionic detergent.

Example 9

The increased robustness for ccfDNA recovery when using different polyoxyalkylene fatty alcohol ethers in the binding mixture was confirmed in a further experimental setup where ccfDNA was isolated from 4 ml Streck stabilized blood plasma using the automated protocol (QIAsymphony) described in Example 8 and using aged magnetic anion exchange beads. As discussed herein, aged anion exchange particles can show a decreased performance after storage which poses a challenging problem. The following non-ionic detergents were tested for their ability to compensate performance variations observed with aged magnetic anion exchange beads:
1. Polyoxyalkylene fatty alcohol ethers
   Brij 58 (2% set as reference to 100% ccfDNA recovery);
   Brij 35;
   Brij 78;
   Brij 98.
2. Other non-ionic detergents
   Triton X-100;
   Igepal C0630;
   Igepal CA720;
   Igepal C0720.

Each detergent was tested in a final concentration in the binding mixture of 2% or 0.5%. Due to solubility limit, Igepal C0630 was only tested in a final concentration of 0.5%. In one set-up, no detergent was included in the binding mixture. Each condition was tested in 2 replicates (n=2).

Figure 11:
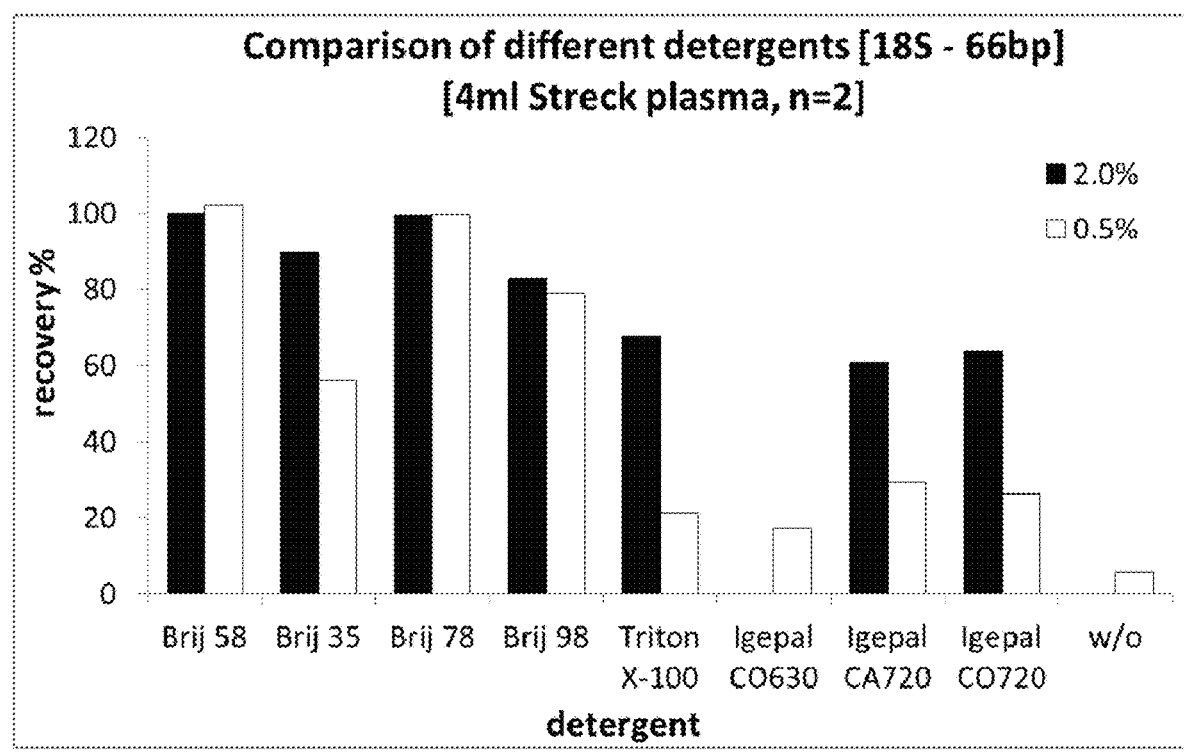
FIG. 11: ccfDNA from 4 ml plasma was extracted using an automated extraction protocol for isolating circulating DNA using aged magnetic anion exchange particles and different non-ionic detergents in the binding mixture. Eluates were subjected to real-time PCR (18S coding sequence; duplex PCR: 66 bp amplicon shown). The results show that the use of polyoxyethylene fatty alcohol ethers in the binding mixture provides superior, more robust results compared to other non-ionic detergents.

The results are shown in FIG. 11. As can be seen, all polyoxyethylene fatty alcohol ethers tested demonstrated good ccfDNA yields even though an aged bead lot was used as anion exchange magnetic particles. In contrast, all other tested non-ionic detergents showed a reduced ccfDNA recovery, in particular when using the detergent in a concentration of 0.5%. In this setting, the ccfDNA recovery dropped below 30%.

Thus, also example 9 demonstrates the advantageous effects that are achieved when using a polyoxyethylene fatty alcohol ether as non-ionic detergent in the binding mixture. Overall, the polyoxyethylene fatty alcohol ether significantly improves the reliability of the ccfDNA isolation because ccfDNA can be recovered consistently with high yield even if variations in the anion exchange surface occur. As discussed, such variations can occur during manufacturing and/or during storage of the solid phase (as it is common when providing materials used in an isolation method in a kit format). The present invention avoids these problems. The improved reliability and improved ccfDNA recovery represent important advantages also considering that the ccfDNA concentration in typical samples, such as e.g. plasma samples, is usually low. Reliable and efficient ccfDNA isolation methods are in particular required for all medical and/or diagnostic applications so that the present invention makes an important contribution. Moreover, a polyoxyethylene fatty alcohol ether as non-ionic detergent is associated with further important advantages, such as an improved storage stability and a high solubility in an aqueous lysis and/or binding composition even if said composition comprises a salt in higher concentration. The reagents/materials used in the present method can therefore be advantageously provided in a kit format. Such kit is advantageously storage stable and thus has a long shelf-life. These advantages are important and are not achieved with other non-ionic detergents.

Example 10

The advantageous performance characteristics with respect to an improved reliability and improved extracellular nucleic acid yield that are achieved when incorporating a polyoxyethylene fatty alcohol ether non-ionic detergent such as Brij 58 in the binding mixture could be continuously demonstrated in multiple experiments. An ongoing performance test used different lots of magnetic anion exchange particles. The results achieved with Brij58 in the binding mixture were tested and compared for each bead lot with the results achieved when using Triton X-100 in the binding mixture.

Table 2 shows the results. The numbers indicate the % recovery compared to the QIAamp Circulating NA Kit (reference—set as 100%). Each bead lot was tested on three consecutive time points (TTP1, TPP2, TPP3) within approx. 1 month after production of the anion exchange particle lot. The tested polyoxyethylene fatty alcohol ether consistently achieved improved yields compared to Triton X-100. Moreover, in contrast to Triton X-100, no significant performance variations were observed between different bead lots when using the polyoxyethylene fatty alcohol ether as non-ionic detergent in the binding mixture. The polyoxyethylene fatty alcohol ether effectively compensated performance variations in the different bead lots. This was not achieved when using Triton X-100 as non-ionic detergent in the binding mixture. With Triton X-100, the overall ccfDNA yields were usually lower compared to Brij58. Moreover, with Triton X-100, significant performance variations were seen with numerous bead lots already within 1 month of storage resulting in recovery rates below 80% (see bead lots 4, 7, 8, 10, 11, 12, 15, 16 and 17 and 21—results under 80% recovery are highlighted). Thus, also example 10 clearly demonstrates the advantageous effects that are achieved when using a polyoxyethylene fatty alcohol ether as non-ionic detergent in the binding mixture.

TABLE 2

| Anion exchange | Brij58 | | | Triton X-100 | | |
|---|---|---|---|---|---|---|
| bead lot tested | TTP1 | TTP2 | TTP3 | TTP1 | TTP2 | TTP3 |
| 1 | 132 | 112 | 175 | 125 | 95 | 169 |
| 2 | 244 | 118 | 164 | 203 | 93 | 146 |
| 3 | 113 | 177 | 115 | 98 | 156 | 113 |
| 4 | 110 | 103 | 100 | 99 | 62 | 41 |
| 5 | 167 | 123 | 118 | 136 | 111 | 106 |
| 6 | 190 | 112 | 126 | 158 | 102 | 106 |
| 7 | 107 | 118 | 87 | 86 | 86 | 78 |
| 8 | 114 | 104 | 93 | 85 | 36 | 19 |
| 9 | 120 | 102 | 117 | 108 | 97 | 109 |
| 10 | 108 | 110 | 100 | 105 | 97 | 71 |
| 11 | 98 | 89 | 87 | 80 | 61 | 56 |
| 12 | 101 | 110 | 91 | 87 | 72 | 57 |
| 13 | 117 | 105 | 107 | 114 | 104 | 112 |
| 14 | 105 | 92 | 100 | 109 | 96 | 91 |
| 15 | 100 | 98 | 114 | 78 | 74 | 80 |
| 16 | 100 | 98 | 88 | 66 | 48 | 44 |
| 17 | 96 | 80 | 113 | 79 | 69 | 89 |
| 18 | 116 | 107 | 113 | 111 | 113 | 112 |
| 19 | 117 | 117 | 110 | 103 | 107 | 103 |
| 20 | 120 | 120 | 113 | 99 | 107 | 93 |
| 21 | 124 | 122 | 125 | 56 | 65 | 61 |

The invention claimed is:

1. A method for isolating extracellular nucleic acids from a biological sample, comprising:
   (a) preparing from the biological sample a binding mixture comprising
      i) extracellular nucleic acids;
      ii) particles providing an anion exchange surface;
      iii) at least one non-ionic detergent selected from polyoxyalkylene fatty alcohol ethers; and
      iv) optionally at least one salt and/or a buffer;
   wherein the binding mixture has a pH so that extracellular nucleic acids bind to the particles, and
   wherein the particles are not comprised in a column,
   (b) separating the particles with the bound extracellular nucleic acids from the remaining binding mixture;
   (c) optionally washing the bound extracellular nucleic acids; and
   (d) optionally eluting bound extracellular nucleic acids.

2. The method according to claim 1, wherein the binding mixture is prepared first by contacting the biological sample with a lysis and/or binding composition which comprises the at least one polyoxyalkylene fatty alcohol ether and optionally comprises a salt and/or a buffer.

3. The method according to claim 1, wherein preparing the binding mixture further comprises contacting the biological sample with a proteolytic enzyme.

4. The method according to claim 1, wherein the binding mixture is prepared by forming a suspension by contacting the particles with a lysis and/or binding composition which comprises the at least one polyoxyalkylene fatty alcohol ether and optionally comprises a salt and/or a buffer;
   contacting the suspension with the biological sample comprising extracellular nucleic acids; and
   optionally adding a proteolytic enzyme prior to, at the same time as or after contacting the biological sample with the suspension.

5. The method according to claim 1, wherein the binding mixture is incubated at conditions for the binding of extracellular nucleic acids, and the biological sample is lysed in the binding mixture.

6. The method according to claim 1, wherein the binding mixture has a pH of ≤7.

7. The method according to claim 1, wherein the binding mixture comprises a salt.

8. The method according to claim 7, wherein
   (a) the salt is an alkali metal salt or an ammonium salt;
   (b) the salt is an alkali metal halide; or
   (c) the salt is comprised in the binding mixture in a concentration of 50 mM to 1.5 M.

9. The method according to claim 1, wherein
   (a) the polyoxyalkylene fatty alcohol ether is a polyoxyethylene fatty alcohol ether;
   (b) the chain length of the fatty alcohol component of the polyoxyalkylene fatty alcohol ether is 8 to 22 carbon atoms;

(c) the polyoxyalkylene fatty alcohol ether comprises a fatty alcohol component having from 14 to 22 carbon atoms and a polyoxyethylene component having from 2 to 150 ($CH_2CH_2O$) units;
(d) the polyoxyalkylene fatty alcohol ether is selected from the group consisting of polyoxyethylene cetyl ether, polyoxyethylene stearyl ether and polyoxyethylene oleyl ether;
(e) the polyoxyalkylene fatty alcohol ether has a critical micelle concentration (CMC) of 0.15 mM or less; or
(f) the binding mixture comprises the polyoxyalkylene fatty alcohol ether in a concentration of 0.05% to 15% (w/v).

10. The method according to claim 1, wherein the anion exchange particles are further not comprised in a device that would prevent the particles from moving in the binding mixture, and wherein the particles are collected from the binding mixture to recover the bound extracellular nucleic acids.

11. The method according to claim 1, wherein
(a) the particles are magnetic;
(b) the particles have a mean diameter in a range of 100 nm to 10 μm; or
(c) the anion exchange surface of the particles comprises anion exchange moieties that provide anion exchange groups, wherein the anion exchange moieties are selected from the group consisting of monoamines, diamines, polyamines, nitrogen-containing aromatic or aliphatic heterocyclic groups, cyclic amines, aromatic amines and heterocyclic amines.

12. The method according to claim 1, wherein the biological sample is:
(a) a cell-free, cell-depleted or cell-containing sample;
(b) selected from the group consisting of whole blood, plasma, serum, synovial fluid, pleural effusion, lymphatic fluid, urine, liquor, cerebrospinal fluid, ascites, milk, bronchial lavage, saliva, amniotic fluid, semen/seminal fluid, body fluids, body secretions, nasal secretions, vaginal secretions, wound secretions or excretions, and derived samples thereof;
(c) selected from the group consisting of whole blood, plasma and serum;
(d) a plasma sample;
(e) a stabilized sample;
(f) stabilized with a formaldehyde releaser; or
(g) a stabilized plasma sample.

13. The method according to claim 1, wherein the method comprises
(a) preparing from the biological sample a binding mixture comprising
  (i) extracellular nucleic acids;
  (ii) magnetic particles providing an anion exchange surface;
  (iii) at least one polyoxyethylene fatty alcohol ether in a concentration of 0.1% to 10% (w/v);
  (iv) at least one alkali metal salt; and
  (v) optionally at least one proteolytic enzyme;
  wherein the binding mixture has a pH ≤6.5 so that extracellular nucleic acids bind to the magnetic particles,
(b) magnetically separating the magnetic particles with the bound extracellular nucleic acids from the remaining binding mixture;
(c) washing the bound extracellular nucleic acids; and
(d) eluting bound extracellular nucleic acids.

14. The method according to claim 1, wherein the method comprises
(a) preparing from the biological sample a binding mixture comprising
  (i) extracellular nucleic acids;
  (ii) magnetic particles providing an anion exchange surface which comprises amine groups;
  (iii) at least one polyoxyethylene fatty alcohol ether in a concentration of 0.1% to 6% (w/v), wherein the polyoxyethylene fatty alcohol ether is selected from the group consisting of polyoxyethylene cetyl ether, polyoxyethylene stearyl ether and polyoxyethylene oleyl ether;
  (iv) at least one alkali metal halide, in a concentration of 100 mM to 1 M; and
  (v) optionally at least one proteolytic enzyme;
  wherein the binding mixture has a pH ≤6.5 so that extracellular nucleic acids bind to the magnetic particles,
(b) magnetically separating the magnetic particles with the bound extracellular nucleic acids from the remaining binding mixture;
(c) washing the bound extracellular nucleic acids; and
(d) eluting bound extracellular nucleic acids.

15. The method according to claim 1, wherein
(a) step (a) of claim 1 further comprises digesting the biological sample at room temperature to release the extracellular nucleic acids;
(b) steps (a) and (b) and optionally (c) and (d) of claim 1 are performed at room temperature; or
(c) a kit comprising the following components is used for performing the method:
  (i) a lysis and/or binding composition comprising or preparing the binding mixture
    (1) at least one polyoxyalkylene fatty alcohol ether;
    (2) at least one salt; and
    (3) at least one buffer;
    wherein said composition has an acidic pH;
  (ii) particles providing an anion exchange surface;
  (iii) optionally a proteolytic enzyme as further component of the binding mixture;
  (iv) optionally one or more wash solutions; and
  (v) optionally one or more elution solutions.

16. A kit for performing the method according to claim 1, comprising:
(a) a lysis and/or binding composition for preparing the binding mixture comprising
  (i) at least one polyoxyalkylene fatty alcohol ether;
  (ii) at least one salt; and
  (iii) at least one buffer;
  wherein said composition has an acidic pH;
(b) particles providing an anion exchange surface, wherein the particles are not comprised in a column;
(c) optionally a proteolytic enzyme as further component of the binding mixture;
(d) optionally one or more wash solutions;
(e) optionally one or more elution solutions; and
(f) a protocol for performing the steps of claim 1.

17. The kit according to claim 16, wherein
(a)
  (i) the polyoxyalkylene fatty alcohol ether is a polyoxyethylene fatty alcohol ether;
  (ii) the chain length of the fatty alcohol component of the polyoxyalkylene fatty alcohol ether is 8 to 22 carbon atoms;
  (iii) the polyoxyalkylene fatty alcohol ether comprises a fatty alcohol component having from 14 to 22 carbon atoms, and a polyoxyethylene component having from 2 to 150 (CH2CH2O) units;

(iv) the polyoxyalkylene fatty alcohol ether is selected from the group consisting of polyoxyethylene cetyl ether, polyoxyethylene stearyl ether and polyoxyethylene oleyl ether; or
(v) the polyoxyalkylene fatty alcohol ether has a critical micelle concentration (CMC) of 0.15 mM or less;
(b) the lysis and/or binding composition comprises the polyoxyalkylene fatty alcohol ether in a concentration of 0.5% to 15% (w/v);
(c)
(i) the salt is an alkali metal salt or an ammonium salt; or
(ii) the salt is an alkali metal halide;
(d) the lysis and/or binding composition comprises the salt in a concentration of 100 mM to 4 M;
(e) the particles have one or more characteristics as defined in claim 11;
(f) the lysis and/or binding composition has a pH in a range of 3 to 6.5; or
(g) the kit comprises a proteolytic enzyme is proteinase K.

18. The method according to claim 1, wherein
(a) step (a) of claim 1 further comprises digesting the biological sample at room temperature to release the extracellular nucleic acids;
(b) steps (a) and (b) and optionally (c) and (d) of claim 1 are performed at room temperature; or
(c) a kit comprising the following components is used for performing the method:
(I)
(i) the polyoxyalkylene fatty alcohol ether is a polyoxyethylene fatty alcohol ether;
(ii) the chain length of the fatty alcohol component of the polyoxyalkylene fatty alcohol ether is 8 to 22 carbon atoms;
(iii) the polyoxyalkylene fatty alcohol ether comprises a fatty alcohol component having from 14 to 22 carbon atoms and a polyoxyethylene component having from 2 to 150 (CH2CH2O) units;
(iv) the polyoxyalkylene fatty alcohol ether is selected from the group consisting of polyoxyethylene cetyl ether, polyoxyethylene stearyl ether and polyoxyethylene oleyl ether; or
(v) the polyoxyalkylene fatty alcohol ether has a critical micelle concentration (CMC) of 0.15 mM or less;
(II) a lysis and/or binding composition for preparing the binding mixture comprises the polyoxyalkylene fatty alcohol ether in a concentration of 0.5% to 15% (w/v);
(III)
(i) the salt is an alkali metal salt or an ammonium salt; or
(ii) the salt is an alkali metal halide;
(IV) a lysis and/or binding composition for preparing the binding mixture comprises the salt in a concentration of 100 mM to 4 M;
(V)
(i) the particles are magnetic;
(ii) the particles have a mean diameter in a range of 100 nm to 10 μm; or
(iii) the anion exchange surface of the particles comprises anion exchange moieties that provide anion exchange groups, wherein the anion exchange moieties are selected from the group consisting of monoamines, diamines, polyamines, nitrogen-containing aromatic or aliphatic heterocyclic groups, cyclic amines, aromatic amines and heterocyclic amines;
(VI) the lysis and/or binding composition for preparing the binding mixture has a pH in a range of 3 to 6.5; or
(VII) the kit further comprises a proteolytic enzyme which is proteinase K as component of the binding mixture.

19. The method of claim 8, wherein the salt is sodium chloride, potassium chloride, or lithium chloride.

20. The method of claim 9, wherein the fatty alcohol component of the polyoxyalkylene fatty alcohol ether is saturated.

21. The method of claim 11, wherein the anion exchange surface comprises anion exchange moieties that comprise at least one primary, secondary and/or tertiary amino group.

22. The method of claim 11, wherein the biological sample is a cell-free or cell-depleted sample derived by removing cells from a sample selected from the group consisting of whole blood, plasma, serum, synovial fluid, pleural effusion, lymphatic fluid, urine, liquor, cerebrospinal fluid, ascites, milk, bronchial lavage, saliva, amniotic fluid, semen/seminal fluid, body fluids, body secretions, nasal secretions, vaginal secretions, wound secretions and excretions.

23. The method of claim 1, wherein the binding mixture comprises the polyoxyalkylene fatty alcohol ether in a concentration of 0.1% to 5% (w/v).

24. The method of claim 1, wherein the extracellular nucleic acids are 500 nucleotides or less in length.

* * * * *

UNITED STATES PATENT AND TRADEMARK OFFICE
CERTIFICATE OF CORRECTION

PATENT NO. : 12,031,125 B2
APPLICATION NO. : 17/385460
DATED : July 9, 2024
INVENTOR(S) : Alexander Wolf et al.

It is certified that error appears in the above-identified patent and that said Letters Patent is hereby corrected as shown below:

In the Claims

Column 38, Claim 15, Lines 31-32:
"(i) a lysis and/or binding composition comprising or preparing the binding mixture"
Should read:
--(i) a lysis and/or binding composition comprising for preparing the binding mixture--.

Column 39, Claim 17, Line 20:
"(g) the kit comprises a proteolytic enzyme is proteinase K."
Should read:
--(g) the proteolytic enzyme is proteinase K.--.

Column 40, Claim 18, Line 20:
"(VI) the lysis and/or
Should read:
--(VI) a lysis and/or--.

Signed and Sealed this
Seventeenth Day of September, 2024

Katherine Kelly Vidal
*Director of the United States Patent and Trademark Office*